(12) United States Patent
Treptow et al.

(10) Patent No.: US 8,374,802 B2
(45) Date of Patent: Feb. 12, 2013

(54) DEVICE AND METHOD FOR RADIOMETRIC MEASUREMENT OF A PLURALITY OF SAMPLES

(75) Inventors: Rainer Treptow, Norderstedt (DE); Gerd Joachim Eckert, Hamburg (DE); Andreas Schirr, Hamburg (DE); Rainer Schliesser, Stuhr (DE); Norbert Wittschief, Achim (DE)

(73) Assignee: Eppendorf AG, Hamburg, DE (US)

( * ) Notice: Subject to any disclaimer, the term of this patent is extended or adjusted under 35 U.S.C. 154(b) by 173 days.

(21) Appl. No.: 12/675,764

(22) PCT Filed: Aug. 29, 2008

(86) PCT No.: PCT/EP2008/007099
§ 371 (c)(1),
(2), (4) Date: Sep. 7, 2010

(87) PCT Pub. No.: WO2009/027102
PCT Pub. Date: Mar. 5, 2009

(65) Prior Publication Data
US 2010/0324834 A1    Dec. 23, 2010

Related U.S. Application Data

(60) Provisional application No. 60/968,671, filed on Aug. 29, 2007.

(51) Int. Cl.
*G01N 31/00* (2006.01)
(52) U.S. Cl. ......................................................... 702/32
(58) Field of Classification Search ...................... 702/32
See application file for complete search history.

(56) References Cited

U.S. PATENT DOCUMENTS

| | | | |
|---|---|---|---|
| 6,197,503 B1 | 3/2001 | Vo-Dinh et al. | |
| 6,852,986 B1 | 2/2005 | Lee et al. | |
| 6,859,275 B2 * | 2/2005 | Fateley et al. | 356/330 |
| 6,888,633 B2 | 5/2005 | Vander Jagt et al. | |
| 7,045,786 B2 * | 5/2006 | Mandelis et al. | 250/341.1 |
| 7,102,131 B2 | 9/2006 | Spolaczyk et al. | |
| 7,148,043 B2 | 12/2006 | Kordunsky et al. | |

FOREIGN PATENT DOCUMENTS

| | | |
|---|---|---|
| EP | 0902271 A2 | 3/1999 |
| JP | 2005-055622 A | 3/2005 |
| WO | WO 98-57153 A1 | 12/1998 |
| WO | WO 01-35079 A1 | 5/2001 |

OTHER PUBLICATIONS

Chance, B., et al., "Phase measurement of light absorption and scatter in human tissue," Review of Scientific Instruments, AIP, 69(10):3457-3481 (1998).

Muschallik, C., "Influence of RF Oscillators on an OFDM Signal," IEEE Transactions on Consumer Electronics, IEEE Service Center, New York, NY 41(3):592-603 (1995).

Scofield, J.H., "Frequency-domain description of a lock-in amplifier," American Journal of Physics, Amercian Assocation of Physics Teachers, US (62(2):129-133 (1994).

* cited by examiner

*Primary Examiner* — Aditya Bhat
(74) *Attorney, Agent, or Firm* — Todd Lorenz; Arnold & Porter LLP

(57) ABSTRACT

The invention relates to a method for photometrically investigating sample radiations of at least one sample, which are caused by the radiation of N emitter elements of at least one radiation element wherein said N emitter elements are emitting radiation during time periods which at least partially overlap, to detect the sample radiation of at least two samples as a sum signal during time periods which at least partially overlap and to evaluate the sample radiation of at least one individual sample from said sum signal.

11 Claims, 19 Drawing Sheets

DEVICE AND METHOD FOR RADIOMETRIC MEASUREMENT OF A PLURALITY OF SAMPLES

The present invention relates to an apparatus and a method for radiometrically investigating a plurality of samples by irradiation wherein the samples respond to said radiation by the emission of sample radiation which is monitored by a detector.

Operating such an apparatus allows to gain the intensity of the sample radiation associated to a specific sample. By the repetitive detection of the sample radiation of a sample at defined times it is possible for instance to analyze the emission of sample radiation as a function of time. An apparatus of this type is used for instance to photometrically test several samples, for example on-line on a thermocycler, in order to quantitatively analyze the progress of a polymerase chain reaction (PCR), preferably in real-time. A further application of such an apparatus may be to probe a plurality of microarray spots on a substrate, or as well wherever multiple samples must be tested radiometrically by means of luminescence, fluorescence, absorption, transmission, scattering phenomena, diffraction, refraction, reflection and the like. The apparatus may be used for on-line sample determination on thermocyclers (for PCR), chip readers, MTP readers, spot readers, and other multi-analytical test means.

Said real-time PCR methods use the fluorescence radiation of at least one type of fluorescence markers in the samples to characterize the progress of the PCR. In the case that several different fluorescence markers are present within one sample, wherein each fluorescence marker has a different excitation spectrum with a maximum at a characteristic excitation frequency, the single radiation spectrum of a single type of radiation element might be adequate to comprise the several excitation frequencies. The U.S. Pat. No. 7,102,131 B2 discloses an apparatus which can be used for real-time PCR and is capable to analyze the fluorescence of several fluorescence indicators in one PCR batch. There is one light source associated to each sample of a sample holder. A drawback of such an arrangement is that the overall radiation energy of said one light source is spread over a continuous spectrum which results in a lower intensity in the required excitation bands. In order to improve the signal/noise-ratio (S/N) of the detected fluorescence radiation it might be appropriate to use light sources with different radiation spectra wherein each radiation spectrum is adapted to sufficiently overlap the excitation spectrum of a specific fluorescence marker respectively. In the case of substantially monochromatic emitter elements, the radiation frequency of a monochromatic emitter element should be sufficiently close to the radiation frequency of the excitation maximum of the corresponding fluorescence marker.

The use of several types of light sources, which each provides a different radiation spectrum, for certain assays requires that each sample is probed by each type of light source. The U.S. Pat. No. 7,148,043 B2 discloses an apparatus for monitoring the fluorescence in a plurality of samples, with a detection unit that provides several excitation/detection channels, each providing a light source which corresponds to a certain fluorescent labeling agent in a sample. Said channels are arranged in a detection module which may be moved along the multiple sample positions of a sample holder by means of stepper motors. Thus, a high number of measuring steps has to be performed in order to scan all the samples. A drawback of such an arrangement is that the positioning error might increase with the number of scanning steps which reduces the reliability of the measured data. In certain screening assays the number of samples provided in well plates is 96, 384 or even 1536. The diameter of a sample chamber decreases with the number of sample positions which even more requires an exact positioning of the detection module to ensure reproducibility and comparability of the data.

Moreover, gathering a plurality of measuring points results in a long overall measuring time in particular for sequential measuring methods as long as the time of a single measurement is not decreased. On the other hand, shortening the time of a single measurement would result in a decrease of the S/N of the detected fluorescence intensity signal. Further, a measuring apparatus which employs the parallel measurement of a very high number of samples, e.g. 96 samples in one parallel measurement, does not mandatory provide a short overall measuring time. Limitations of the effectiveness of such a massive parallel measurement occur because of the errors involved with the limited bandwith of the used signals and the limited computation power for the transformation operations which are related to the evaluation of the measured signals. Thus, the decrease of measurement time and the improvement of the S/N of the measured signal requires additional effort.

It is an object of the present invention to provide an improved apparatus for radiometrically investigating a plurality of samples, wherein the apparatus in particular offers a shortened overall measuring time and/or achieves a good S/N of the detected signals of sample radiation. It is further an aspect of the object of the present invention to provide another method to measure radiometrically a plurality of samples.

The present invention achieves said object by providing a method, an apparatus, a computer code, and a storage medium according to the claims as filed. Preferred developments of the present invention are subject matter of the sub-claims.

According to one embodiment of the present invention, a method for radiometrically investigating N (N is a natural number with N>1) sample radiations of at least two samples, which are caused by the radiation of N emitter elements of at least one radiation element wherein said N emitter elements are emitting radiation during time periods which at least partially overlap, comprises the steps:
determining a set of N basic frequencies,
adding one reference frequency to each of said basic frequencies wherein said reference frequency is higher than each of said basic frequencies,
using the N sums of the reference frequency and of the basic frequency to provide N modulation signals wherein each modulation signal is used to modulate the radiation of a different emitter element,
detecting the N sample radiations as a sum signal wherein each sample radiation is modulated according to the modulated radiation which caused the respective sample radiation,
demodulating the sum signal by using a demodulation method,
performing a transformation to transfer the demodulated sum signal from a time dependent signal into a frequency dependent signal, and
determining the quantity of at least one individual sample radiation from the amplitude of said frequency dependent signal in dependence on the basic frequency.

Demodulation of the sum signal is performed preferably by a multiplication process, which in particular multiplies the sum signal with the reference frequency. Thus, demodulating the sum signal preferably means a down-mixing of the sum signal. The demodulation is preferably performed by using analogue electronics means, e.g. a ring modulator, and is preferably performed by using digital electronic means.

Said method according to the present invention offers the particular advantage that the radiation signal which is modulated by the modulation signal and a potential interfering signal, which can be in particular a low frequency interference, have a different time characteristics, which reduces the disturbing of the radiation signal by the potential interfering signal. In particular, the frequency band which is used for the modulation, is shifted to higher frequencies compared with the frequencies of potential interference signals. Thus, the interferences are avoided and the S/N of the detected quantity of a sample radiation is improved. Moreover, by using different modulation signals, it is possible to address a specific emitter of sample radiation, e.g. a fluorescence marker, or to address a specific sample of the plurality of samples. By said addressing, the sample radiation of a specific emitter of sample radiation or a specific sample becomes discriminable within the sum of N sample radiations which is detected. In contrast to a sequential operation of detection of N sample radiations, the parallel measuring of N different sample radiations offers the possibility to reduce the overall detection time of said N sample radiations which means that the overall measuring time can be reduced.

Said N basic frequencies are preferably substantially equidistant and are preferably chosen from a frequency range of 0 kHz to 4 kHz. However, it is possible and preferred that said N basic frequencies are not substantially equidistant. Moreover, it is possible and preferred that said N basic frequencies are in the range from 4 KHz to 1 MHz.

The reference frequency is preferably chosen to be much higher than a basic frequency, e.g. to be at least a basic frequency multiplied by the factor 2 or preferably at least a magnitude higher than the basic frequency. A preferred frequency range of the reference frequency is further 80 kHz to 120 kHz Preferably the reference frequency is 100 kHz. However, the reference frequency can be different, as described above.

It is possible and preferred that instead of the frequency division multiple access (FDMA) method at hand, another FDMA method is used to modulate the radiation of at least two radiation elements during time periods which at least partially overlap and to evaluate the sum of sample radiations which is caused by said at least two radiation elements.

The sum signal of N sample radiations which is generated by a detection device is preferably amplified by a transimpedance amplifier. Said transimpedance amplifier is preferably a device which converts a current to a voltage signal. In this case, the sum signal is a current signal, which is converted to a voltage signal by said transimpedance amplifier. Preferably, the transimpedance amplifier has a high-pass function which is capable to suppress low-frequency interferences (noise) of the sum signal at least partially.

The sum signal is preferably filtered by a high-pass filter, in particular a digital high-pass filter. This has the advantage that interfering signals of low frequency are not regarded in the evaluation process and thus, the S/N of the detected quantity of sample radiation is improved.

Said quantity of at least one individual sample radiation from the decoded sum signal preferably is a signal amplitude which is a measure of the strength of the sample radiation which was addressed by said modulation frequency.

Using the explanations and definitions of the description of the present invention, the following embodiments of the method according to the present invention are provided.

In a preferred embodiment, a method according to the present invention for radiometrically investigating a plurality of samples, preferably comprises the steps: irradiating at least partially simultaneously a number of N samples of the entirety of samples, said N samples comprising at least one first group and at least one second group of samples, each group including at least two samples, said first group of samples being irradiated by radiation of a first spectrum, and said second group of samples being irradiated by radiation of a second spectrum, wherein each of said at least one first and one second spectra of an entirety of n spectra are different, wherein each sample within each group of samples is irradiated by radiation of different modulation; and detecting at least partially simultaneously the sample radiation of said N samples.

Preferably the method according to the present invention comprises the steps of: providing an entirety of x*y sample positions or samples, arranged in an array of x rows and y columns, each sample position being adapted to hold a sample; providing an array of radiation elements, which is arrangable such that each radiation element is at least intermittently assigned to one sample, the array consisting of r=x+n−1 rows (r>=x) and c=y columns wherein the radiation elements of each row show the same row-emission spectrum which is one out of said n different emission spectra and wherein further m blocks of rows are provided, wherein a number (the number >0) of blocks have the same sequence of rows with row-emission spectra (r, c, n and m are natural numbers).

Preferably the method according to the present invention comprises the step of: let at least a column of at least r=x radiation elements irradiate at least partially simultaneously, in particular simultaneously, said corresponding x samples, wherein said N=x.

Preferably the method according to the present invention comprises the steps of: performing at least partially simultaneously, in particular simultaneously, the previously described step for each column of radiation elements and corresponding samples.

Preferably the method according to the present invention comprises the steps of: splitting the sample radiation of said N samples into spectral components, each component representing the sample radiation, which corresponds to one of said groups of samples; and transmitting each of said components of sample radiation towards a detection unit.

Preferably the method according to the present invention comprises the step of: demodulating said sum signal and evaluating the sample radiation of each individual sample of said N samples.

Preferably the method according to the present invention comprises the steps of: providing a total number of, in particular n−1, positioning steps of the radiation device relative to the sample holder member, in order to perform a complete scan of the samples by each type of radiation element.

Further, using the explanations and definitions of the description of the present invention, the following embodiments of the method according to the present invention are provided.

The method according to the present invention wherein said N basic frequencies are chosen from a frequency range of 0 kHz to 1 MHz.

The method according to the present invention wherein said reference frequency is at least an order of magnitude higher than each of said basic frequencies.

The method according to the present invention wherein it comprises a step of filtering the detected sum signal by a highpass filter.

The method according to the present invention wherein it comprises a step of filtering the detected sum signal by a bandpass filter.

The method according to the present invention wherein it comprises a step of digitising said sum signal by sampling with a sampling frequency and quantizing.

The method according to the present invention wherein the sampling frequency is equal or higher than the nyquist frequency.

The method according to the present invention wherein it comprises a step of averaging said sum signal over the time.

The method according to the present invention wherein it comprises a step of filtering said sum signal by a digital high-pass filter prior to demodulation.

The method according to the present invention wherein a demodulation method demodulates the sum signal by multiplying it with the reference frequency, The method according to the present invention wherein a step of sub-sampling is performed after demodulation of the sum signal.

The method according to the present invention wherein said transformation operation is a mathematical operation.

The method according to the present invention wherein said transformation operation is a fourier transformation method.

In analogy to said method, an apparatus for radiometrically investigating N (N is a natural number with N>1) sample radiations of at least two samples, which are caused by the radiation of N emitter elements of at least one radiation element wherein said N emitter elements are emitting radiation during time periods which at least partially overlap, comprises:

a control device, adapted to control said radiation elements and to use N basic frequencies to provide N modulation signals wherein each modulation signal is used to modulate the radiation of a different emitter element, at least one detection device which is adapted to detect the sample radiation of at least two samples as a sum signal during time periods which at least partially overlap, an evaluation device which is adapted to evaluate the sample radiation of an individual sample from said sum signal, wherein the evaluation device is adapted to demodulate the sum signal, to perform a transformation operation to transfer the demodulated sum signal from a time dependent signal into a frequency dependent signal, and to determine the quantity of at least one individual sample radiation from the amplitude of said frequency dependent signal in dependency on the basic frequency.

According to another embodiment of the present invention, a method for radiometrically investigating N (N is a natural number with N>1) sample radiations of at least one sample, which are caused by the radiation of N emitter elements of at least one radiation element wherein said N emitter elements are emitting radiation during time periods which at least partially overlap, comprises the steps:

determining one code sequence of pseudorandom numbers, modulating the radiation which is to be emitted by each of said N emitter elements with an individual modulation signal which is formed by using said one code sequence of pseudorandom numbers, wherein the pseudorandom number code of an individual modulation signal is shifted about at least one bit against the pseudorandom number codes of the other modulation signals, detecting the N sample radiations as a sum signal wherein each sample radiation is modulated according to the modulated radiation which caused the respective sample radiation, performing a mathematical operation on said sum signal to decode it, determining the quantity of at least one individual sample radiation from the decoded sum signal.

Said method according to the present invention offers the particular advantage that the radiation signal which is modulated by the modulation signal and a potential interfering signal, which can be in particular a low frequency interference, have a different time characteristics, which reduces the disturbing of the radiation signal by the potential interfering signal. In particular, the frequency band which is used for the modulation, is positioned at much higher frequencies compared with the frequencies of potential interference signals. Thus, the S/N of the detected quantity of a sample radiation is improved. Moreover, by using different modulation signals, it is possible to address a specific emitter of sample radiation, e.g. a fluorescence marker, or to address a specific sample of the plurality of samples. By said addressing, the sample radiation of a specific emitter of sample radiation or a specific sample becomes discriminable within the sum of N sample radiations which is detected. In contrast to a sequential operation of detection of N sample radiations, the parallel measuring of N different sample radiations offers the possibility to reduce the overall detection time of said N sample radiations which means that the overall measuring time can be reduced.

The code sequence of said pseudorandom numbers is preferably a Gold-code. However, it is possible and preferred that said code sequence is chosen from other sequences which are used in spread spectrum systems, e.g. maximal length sequences, Kasami sequences, Barker codes and the like. The length of the code is preferably at least $2^{N-1}-1$, where N is the number of samples to be monitored during time periods which at least partially overlap.

For the description of code sequences and other technical terms it is referred to the book of Don Torrieri "Principles of spread-spectrum communication systems", Springer, 2005, which is incorporated herein by reference.

It is possible and preferred that another code division multiple access (CDMA) method is used to modulate the radiation of at least two radiation elements during time periods which at least partially overlap and to evaluate the sum of sample radiations which is caused by said at least two radiation elements.

The evaluation device preferably comprises a decoding device, e.g. a correlator device or a multiplicator device, for performing said mathematical operation which is the decoding operation. The decoding operation preferably comprises a correlation operation, e.g. autocorrelation, or a multiplication, to resolve the quantity of the sample radiation from said sum signal.

It is a particular advantage of using said correlation method that the hardware implementation of said correlation method is easier and the calculation time which is required to apply said correlation method can be reduced compared with an FFT operation.

Using the explanations and definitions of the description of the present invention, the following embodiments of the method according to the present invention are provided:

The method according to the present invention wherein the code sequence of pseudorandom numbers is a Gold-code.

The method according to the present invention wherein the mathematical operation comprises a correlation method for correlating the sum signal with an individual modulation signal.

The method according to the present invention wherein said correlation method is autocorrelation-type.

The method according to the present invention wherein said mathematical operation substantially is substitutable by addition and subtraction operations.

In analogy to said method, an apparatus for radiometrically investigating N (N is a natural number with N>1) sample radiations of at least one sample, which are caused by the radiation of N emitter elements of at least one radiation element wherein said N emitter elements are emitting radiation during time periods which at least partially overlap, comprises:

a control device, adapted to control said radiation elements and to modulate the radiation which is to be emitted by each of said N emitter elements with an individual modulation signal which is formed by using said one code sequence of pseudorandom numbers, wherein the pseudorandom number code of an individual modulation signal is shifted about at least one bit against the pseudorandom number codes of the other modulation signals, at least one detection device which is adapted to detect the sample radiation of at least one samples as a sum signal during time periods which at least partially overlap, an evaluation device which is adapted to evaluate the sample radiation of an individual sample from said sum signal, wherein the evaluation device is adapted to decode said sum signal by a mathematical operation, and wherein the evaluation device is adapted to determine the quantity of at least According to a further embodiment, a method for radiometrically investigating N (N is a natural number with N>1) sample radiations of at least one sample, which are caused by the radiation of N emitter elements of at least one radiation element wherein said N emitter elements are emitting radiation during time periods which at least partially overlap, comprises the steps:

determining a set of N Hadamard-code-sequences wherein each of said Hadamard-code-sequences is used to form an individual modulation signal, modulating the radiation which is to be emitted by each of said N emitter elements with a different individual modulation signal, detecting the N sample radiations as a sum signal wherein each sample radiation is modulated according to the modulated radiation which caused the respective sample radiation, performing a mathematical operation on said sum signal to decode it, determining the quantity of at least one individual sample radiation from the decoded sum signal.

Said method according to the present invention offers the particular advantage that the radiation signal which is modulated by the modulation signal and a potential interfering signal, which can be in particular a low frequency interference, have a different time characteristics, which reduces the disturbing of the radiation signal by the potential interfering signal. In particular, the frequency band which is used for the modulation, is positioned at much higher frequencies compared with the frequencies of potential interference signals. Thus, the S/N of the detected quantity of a sample radiation is improved. Moreover, by using different modulation signals, it is possible to address a specific emitter of sample radiation, e.g. a fluorescence marker, or to address a specific sample of the plurality of samples. By said addressing, the sample radiation of a specific emitter of sample radiation or a specific sample becomes discriminable within the sum of N sample radiations which is detected. In contrast to a sequential operation of detection of N sample radiations, the parallel measuring of N different sample radiations offers the possibility to reduce the overall detection time of said N sample radiations which means that the overall measuring time can be reduced.

Said correlation method is preferably autocorrelation-type and preferably backtransforms the sum of N sample radiations using the Hadamard-Matrix which comprises said N Hadamard-code-sequences. In particular, a Walsh-Hadamard-Transform can be used. It is a particular advantage of using said correlation method that the hardware implementation of said correlation method is easier and the calculation steps which are required to perform said correlation method can be performed faster compared with a classic FFT analysis. In a preferred embodiment, signal analysis is performed by a matrix multiplication of the signal vector with the inverse Hadamard Matrix $H^{-1}$. $H^{-1}$ can be calculated once from the Hadamard sequence matrix H and may be stored fixed in the operational software or data memory. This allows for a universal applicability of the method and an easy implementation.

Using the explanations and definitions of the above description of the method according to the present invention, the following embodiments of the method according to the present invention are provided:

The method according to the present invention wherein said Hadamard-code-sequences are orthogonal.

The method according to the present invention wherein the mathematical operation comprises a correlation method for correlating the sum signal with an individual modulation signal.

The method according to the present invention wherein said correlation method is autocorrelation-type.

The method according to the present invention wherein said mathematical operation substantially is substitutable by addition and subtraction operations.

The method according to the present invention wherein said correlation method backtransforms the sum signal by using the inverse Hadamard-Matrix which is related to said N Hadamard-code-sequences.

The method according to the present invention wherein said correlation method uses a Walsh-Hadamard-Transform.

In analogy to said method, an apparatus for radiometrically investigating N (N is a natural number with N>1) sample radiations of at least one sample, which are caused by the radiation of N emitter elements of at least one radiation element wherein said N emitter elements are emitting radiation during time periods which at least partially overlap, comprises:

a control device, adapted to control said radiation elements and to modulate the radiation of said N emitter elements by a set of N Hadamard-code-sequences wherein each of said Hadamard-code-sequences is used to form an individual modulation signal, at least one detection device which is adapted to detect the sample radiation of at least one samples as a sum signal during time periods which at least partially overlap, an evaluation device which is adapted to evaluate the sample radiation of an individual sample from said sum signal, wherein the evaluation device is adapted to decode said sum signal by a mathematical operation, and wherein the evaluation device is adapted to determine the quantity of at least one individual sample radiation from the decoded sum signal.

The methods according to the present invention offer the advantage that the measurement is less sensitive for extraneous light which might interfere with the detected sample radiations. Generally, the interference liability is reduced by the methods according to the present invention. In particular, the inherent noise of the detection unit can be suppressed at least in part by the methods according to the present invention.

According to a further embodiment, an apparatus for radiometrically investigating a plurality of samples comprises:
a radiation device providing at least one radiation element and at least two emitter elements, wherein each radiation element comprises at least one emitter element and wherein said at least two emitter elements are adapted to emit radiation during time periods which at least partially overlap, a control device, controlling said radiation device, a sample holder member providing a plurality of sample positions for supporting a plurality of samples, wherein at least a part of the radiation device and the sample holder member are adapted to be moved against each other during the investigation procedure and wherein each of said at least two emitter elements is adapted to irradiate a different sample with radiation via a first optical path which causes the sample to emit sample radiation with at least one sample radiation frequency via a second optical path towards at least one detection device, said at least one detection device being adapted to detect the sample radiation which is emitted by at least two samples during time periods which at least partially overlap as a sum signal; and an evaluation device which is adapted to evaluate the sample radiation of at least one individual sample from said sum signal.

According to another embodiment, an apparatus for radiometrically investigating a plurality of samples comprises:
a radiation device providing at least one radiation element and at least two emitter elements, wherein each radiation element comprises at least one emitter element, wherein said at least two emitter elements are adapted to emit radiation during time periods which at least partially overlap, and wherein a minimum of two emitter elements provide radiation with different radiation spectra, a control device, controlling said radiation device, a sample holder member providing a plurality of sample positions for supporting a plurality of samples, wherein each of said at least two emitter elements is adapted to irradiate at least one sample with radiation via a first optical path which causes the sample to emit sample radiation with at least one sample radiation frequency via a second optical path towards at least one detection device, said at least one detection device being adapted to detect the sample radiation which is emitted by at least two samples during time periods which at least partially overlap as a sum signal; and an evaluation device which is adapted to evaluate the sample radiation of at least one individual sample from said sum signal.

The term "plurality" means "a minimum of two" in the context of the present invention.

An emitter element can be formed as radiation source. A radiation source may be taken from a group of radiation sources comprising LEDs, high-power-LEDs, OLEDs, laser diodes and the like. A radiation source can further be an SMD-LED which in particular offers the advantages of a low spatial dimensioning and high mechanical stability against vibrations. Other suitable radiation sources may comprise all those emitter elements fit for radiometry that may be selected depending on the requirements on radiation, for instance for fluorescence purposes, or depending on the requirements set on the radiation path, for instance sharp focusing on one of several samples, or regarding radiation intensity or durability and dimensioning of the radiation element. Accordingly, also incandescent bulbs and laser, flash, terahertz radiation sources, other sources of electromagnetic radiation as well as sources of particle radiation, e.g. beta radiation, are applicable.

It is further possible and preferred that an emitter element is formed as optical path means wherein the emitter element preferably does not comprise a radiation source but comprises means for affecting the optical path of the radiation which is emitted by at least one radiation source. The radiation source in this case is preferably separated from the emitter element. Preferably the emitter element is a device which comprises the end face of an optical fiber. Such an optical fiber can be used to transmit radiation from at least one radiation source to an emitter element. Preferably only a few radiation sources, e.g. of only one radiation source whose radiation is transmitted to a plurality of emitter elements via a bundle of optical fibers, are operated. An advantage of this configuration is that the number of radiation sources can be smaller than the number of emitter elements which means that less cost is involved in operation and maintenance of the radiation device. Furthermore, the quality of the measured data is improved, because the error, which might result from using several radiation sources with individual characteristics, e.g. intensity, spectrum, temperature dependence and the like, is reduced to the error of one radiation source. In consequence, the measured data gain reliability and comparability.

A radiation element can further comprise at least one optical supplementary means like an optical filter, fiber, lens, mirror and the like, to modify the radiation of the radiation element.

Preferably at least one input port is provided with the apparatus, in particular with the radiation device, wherein said input port is adapted to receive the radiation, which is to be transmitted towards at least one radiation element, which in consequence have the same emission spectrum. This is in particular preferred, if the number of radiation sources is smaller than the number of emitter elements. Preferably, each input port is adapted to receive the radiation of a radiation source, in particular the radiation of a different radiation source. The distribution of radiation from the input ports to the radiation elements or emitter elements is preferably at least partially realized by fiber optics. It is further possible and preferred that the distribution of radiation from the input ports to the emitter elements is at least partially realized by integrated optics, e.g. based on polydimethylsiloxane (PDMS).

It is further possible and preferred that a radiation element comprises several emitter elements whose radiation superimposes to form one radiation, for example a radiation element comprising a plurality of LEDs.

The spectrum of the radiation which is emitted by an radiation element is preferably narrowband or substantially monochromatic. It is further preferred that an emitter element of a radiation element emits a narrowband or substantially monochromatic radiation. This can be the case for example for LEDs which are preferably applied as emitter element and which offer the advantage that the radiant flux is concentrated on a relatively small range of wavelength. Such a narrowband radiation can cause for instance in fluorescence applications a higher yield of fluorescence light than a broadband radiation of the same flux.

Further, it is possible and preferred that the spectrum of the radiation which is emitted by a radiation element comprises a broader range of wavelengths. Such a broadband spectrum offers the advantage that in processes which are caused in dependence on different wavelength bands, several processes can be initiated by one excitation radiation which covers the different wavelength bands. Fluorescence is an example for such a process wherein one broadband radiation is able to excite the fluorescence of different fluorescent markers which have different excitation spectra. In this configuration, the emitter element of a radiation element is preferably emitting white light which might in particular be emitted by a white high-performance-LED. Moreover it is preferred to provide several light sources which in combination form a white light source, for example several light sources of different spectra which are mounted in parallel within one radiation element, for instance a yellow, red, green and blue LED respectively in parallel which set up a broadband emitter element or radiation element.

The emitter elements of a specific radiation element or of different radiation elements preferably emit radiation during time periods which at least partially overlap or emit sequentially.

Radiation in the context of this invention preferably means electromagnetic radiation. Preferably, the electromagnetic radiation is visible light, UV-light or infrared light and the sample radiation preferably is fluorescence light. Said fluorescence light may be emitted from fluorescence markers which are preferably appropriate to be used for the quantitative analysis in a PCR and are preferably chosen from a group of fluorescence markers that includes ethidium bromide, cyanine dyes (e.g. SYBR Green I®), FRET-probes (e.g. Light-Cycler®- or TaqMan®-probes), fluorescent nanoparticles and the like. It is further possible that the radiation is terahertz radiation which substantially refers to the frequency range of 300 GHz to 10 THz.

However, the radiation can also be a particle radiation, e.g. beta radiation which upon irradiation of a sample causes any type of sample radiation.

The radiation preferably runs along a first optical path from the emitter element and is transmitted to a sample where it causes a sample radiation. The sample radiation runs from the sample via a second optical path towards the detector device. The first and the second optical path may at least partially overlap, may completely overlap, or may not overlap.

The radiation device preferably comprises an arrangement of radiation elements. Said arrangement is preferably an array of preferably periodically arranged radiation elements which preferably are mounted on at least one substrate. The alignment of said array is preferably substantially one dimensional, is preferably substantially two-dimensional, in particular in parallel to the sample holder member, but can be as well at least partially three-dimensional aligned. Other devices like controllers, sensors, circuits, passive or active cooling elements might be comprised as well by the radiation device.

The radiation device preferably provides narrowband radiation of at least two different radiation spectra. It is possible and preferred that at least two radiation elements or emitter elements of the plurality of radiation elements provide a different radiation spectrum wherein preferably each of said radiation spectra is adapted to optimally excite a different fluorescence marker respectively.

In the following, the preferred orientation and alignment of parts of the apparatus is explained using a Cartesian coordinate system. Within said system, the x-y plane hereinafter refers to the horizontal plane, while the positive z-direction means "upward". The radiation device is preferably arranged at least in part movably respective to—and preferably at least partially in parallel to—the sample holder member which is preferably arranged in the x-y-plane. The radiation device preferably comprises a support member which supports said at least one substrate on which said at least two radiation elements are mounted. Said substrate is preferably mounted movably relative to said support member and is preferably mounted rotatable around an axis of rotation, which can be aligned in parallel or perpendicular to the sample holder member. Thus, said at least one radiation element and said at least two emitter elements can be mounted space-saving. Preferably, x-motion means and/or y-motion means are provided which can move the radiation device respective to the sample holder member along the x- and/or y-direction. Additionally, pivoting motion means can be provided which allow an angular motion of the radiation device relative to the sample holder member. In this case, the axis of rotation can be parallel or perpendicular to the main plane of the sample holder member. Preferably, the radiation device is arranged in a predetermined distance to the sample holder member. Said distance is preferably adjustable by z-motion means which can move the radiation device respective to the sample holder member along the z-direction. The x-, y- and z-motion means preferably comprise a step motor and/or a piezo actuator and are preferably controlled by the control device, other supplementary control devices or at least partially by the manual control of a user.

The apparatus preferably provides locking means in combination with the x-, y-, z- and/or pivoting motion means to more precisely define the position of the radiation device respective to the sample holder member for each motion step. The locking means can be a locking or a spring-mounted locking at the radiation device which positive engages a corresponding pit of a plurality of pits which are aligned to define locking positions at the apparatus. However, any locking means which is capable to arrest and preserve the position of the radiation device relative to the apparatus can be used. Thus, the re-positioning of a sample respective to a radiation element is improved, which enhances the reliability of the measured data.

Further, the radiation device is preferably at least partially arranged on top of the sample holder device, i.e. inside the half space of the x-y-plane in direction of the positive z-axis. This allows to direct the radiation downwards into a sample receptacle which is upside transparent for the radiation.

Moreover it is possible and preferred that the radiation device is at least partially arranged under the sample holder device. The latter configuration as well offers advantages for certain setups and experiments. First, the space on top of the sample holder device is available for other technical devices of the apparatus. Moreover, in the case that for example the bottom of a sample receptacle containing a liquid sample is transparent for light, the radiation does not have to pass the meniscus of the sample. The meniscus of a liquid and transparent sample acts like a lens for light. Since the shape of the meniscus is different for all the samples, the light path through the different samples will differ slightly which causes deviations in the interaction of the respective beam of radiation with the sample and causes further an error in the measured data. Thus, it is beneficial for the reproducibility of the measurements to transmit the radiation through a transparent bottom of the sample receptacle and through the planar interface between the bottom and the sample liquid which allows a more precise control over the radiation path.

According to the present invention, said at least two emitter elements are emitting radiation during time periods which at least partially overlap. This means that at least two emitter elements emit radiation at least partially simultaneously. It further means that there is at least one intersectional time period during which all of said at least two emitter elements emit a continuous radiation, i.e. during which the quantities of the radiations which are emitted by all of said at least two emitter elements are larger than null. Thus, a purely alternating operation of emitter elements, e.g. combined with a pulsed operation, is not rated as "at least partially simultaneously". In particular, "at least partially simultaneously" means, that said time periods can have different lengths and can have different start and/or end times. Moreover, said time periods can be the same. "At least two emitter elements emit radiation at least partially simultaneously" further means that said at least two emitter elements are active during time periods which at least partially overlap. The term "active emitter element" hereinafter means that said emitter element is emitting radiation.

The active period of an emitter element is preferably adjustable and controlled in dependence on the yield or the S/N of the detected sample radiation. Thus, the overall activity time for at least two single emitter elements is shortened in comparison to a sequential activity for said at least two radiation elements which means that the overall measuring time of the apparatus is reduced. Further, for a predetermined S/N the overall measuring time can be reduced. Moreover, the reduction of the overall activity time of the emitter elements can lead to a reduced radiative load on the samples which for example in the case of sample fluorescence might avoid an actinic damage of a fluorescence marker. Also the lifetime of the radiation sources might be extended which reduces maintenance of the apparatus. Alternatively and preferred, the additional lifetime and the additional recovery time of the radiation sources may be used to operate the at least one radiation source over the specification of said radiation source, for instance to operate an LED at least intermittently with a higher current than the specified continuous current.

The radiation device preferably is movably arranged relative to the sample holder member. This means, it is preferably at least possible to move the radiation device against the sample holder member from a first position wherein the apparatus gets loaded with samples, to a second position wherein the photometric measurement of the samples can occur. Moreover, it is possible and preferred, that within said second position, at least part of the radiation device is movably arranged relative to the sample holder member in order that a scanning motion being able to be performed stepwise.

Preferably, the radiation device is at least intermittently arranged such that a plurality of radiation elements can irradiate a same number of samples wherein each radiation element substantially irradiates one—at least intermittently corresponding—sample. Thus, the radiation device is preferably able to irradiate a substantial fraction of the samples, in particular all samples of the sample holder member, without having to be moved. As an advantage, the overall positioning error and the mechanical stress on the apparatus are reduced which decreases the maintenance requirements of the apparatus while increasing its lifetime. Further, a parallel measuring of a plurality of samples, which is preferred, is allowed by this arrangement. The parallel measuring of several samples allows to shorten the overall measuring time and allows in particular to extend the time of detecting sample radiation from individual samples to improve the S/N of the sample radiation. It is further possible and preferred, that said at least two emitter elements irradiate the same number of samples or another number of samples, which can be higher or lower, preferably aided by additional optical means which are preferably arranged at the emitter elements. Thus, it is possible that the radiation which is emitted by a radiation element and its respectively at least one emitter element is guided to one or more samples, preferably via said first optical path, wherein said first optical path is preferably aligned perpendicular to the sample holder member but can also preferably at least partially follow a non-perpendicular, e.g. angular or bended direction as well.

Preferably, the radiation device provides a plurality of radiation elements which are arranged at periodical positions in an array. Preferably, the array consists of r rows and c columns, wherein r and c are natural numbers with preferably $r>1$ and $c>1$. Alternatively it is preferred that either $r>1$ and $c=1$ or preferably $r=1$ and $c>1$. The arrangement of radiation elements preferably corresponds geometrically to the arrangement of samples.

Further, a plurality of radiation elements is preferably arranged in an array wherein preferably at least one pattern composed of at least two different radiation elements which have at least two different emission spectra respectively is repeated at least once. At least two different radiation elements having at least two different emission spectra means that said at least two radiation elements are adapted to provide at least two emitter elements which provide radiation with different radiation spectra. Said pattern is preferably any sequence of radiation elements which have at least two different emission spectra, is preferably a linear sequence and is preferably a planar assembly. An advantage of using at least one repeated pattern is that for certain measurement assays the number of required positioning steps of the radiation device relative to the sample holder member can be minimized. Minimizing the number of positioning steps leads to a reduction of the overall positioning error and the mechanical stress on the apparatus which decreases the maintenance requirements of the apparatus while increasing its lifetime. Further, the step size of the positioning steps can be reduced with an periodical arrangement of radiation elements whereby also the overall measuring time is reduced and the demands on the capacity and dimension of the motion means which perform the said positioning steps are diminished.

Preferably, the array consists of r rows and c columns, wherein r and c are natural numbers with preferably $r>1$ and $c>1$. In the case that the number of different types of radiation-elements which are used for the radiation device is n, for example due to n different radiation spectra comprised by the radiation elements, wherein n is a natural number and $n>1$, it is preferred that the number of rows is $r=n$. It is further preferred that a row comprises one type or the same type of radiation elements to form a row with a row-emission spectrum. Such a row-wise geometry in particular allows to simply design auxiliary means which provide a corresponding row-wise geometry to direct the sample emission row-wise to the detector device. Further, the scanning of the samples by stepwise moving of the sample holder member can be limited to one direction, for example the x-direction, thus requiring less effort in the design of the motion means compared to a two-directional scanning.

Preferably, the number of columns of the array of the radiation device has the same number of columns as the array of sample positions of the sample holder member, which is defined by x rows multiply y columns, which can be expressed by $y=c$. In this case, the number of rows of the array of the radiation device is preferably n (i.e. $r=n$), wherein preferably each row has a specific row-emission spectrum. By such an arrangement, the number of positioning steps can be reduced to $x+n-2$, once the radiation device is positioned in its first position, in order to perform a complete scan of the samples by each type of radiation element.

It is further preferred that said array of the radiation device consists of the product of r=n*m rows and c columns wherein each row has one row-emission spectrum out of n different row-mission spectra and wherein further m blocks of rows are provided, each block having the same sequence of rows with row-emission spectra, wherein m is a natural number with m>1. Such a block-wise arrangement of radiation elements allows to reduce the number of scanning steps. It is further possible and preferred, that m blocks are provided wherein each block of rows has one type of row with a block-wise row-emission spectrum. Such a block-wise geometry allows to simply design auxiliary means which provide a corresponding block-wise geometry to direct the sample emission block-wise to the detector device.

Preferably, the array of radiation elements consists of r=(n*m)−1 rows and c columns wherein the radiation elements of each row show the same row-emission spectrum which is one out of n different emission spectra and wherein further m blocks of rows are provided, wherein m−1 blocks have the same sequence of rows with row-emission spectra (r, c, n and m are natural numbers) and one block has said sequence in part. In this case, the radiation device preferably provides a number of radiation elements which is the same as the number of sample positions of the sample holder member, plus additional n−1 rows of radiation elements. By such an arrangement, the number of positioning steps can be reduced to n−1, once the radiation device is positioned in its first position, in order to perform a complete scan of the samples by each type of radiation element.

Preferably, the array of radiation elements consists of r=n*m rows and c columns wherein a plurality of blocks with m rows each are provided, wherein the radiation elements of each block show the same block-emission spectrum which is one out of n different emission spectra (r, c, n and m are natural numbers). In this case, the number c of columns of the radiation device and the number x of columns of the array of sample positions of the sample holder member are the same. By such an arrangement, the number of positioning steps can be reduced to (x/m)+n−2, once the radiation device is positioned in its first position, in order to perform a complete scan of the samples by each type of radiation element.

Further, it is preferred that the array of radiation elements has r rows and c columns with r>=12 and c>=8, r>=24 and c>=16, or r>=48 and c>=32, which corresponds to standard well plate configurations respectively.

Preferably the number of radiation elements exceeds the number of sample positions which are provided by the sample holder member. The difference of the number of radiation elements and the number of sample positions is preferably n*c wherein n and c are defined as stated above. An advantage of this configuration is that in each positioning step of the radiation device relative to the sample holder member an association between one radiation element and one sample can be established which allows a highly parallel measuring. Preferably, in each positioning step one row of samples is associated to a different row of radiation elements with a row-radiation frequency.

The auxiliary device of the apparatus according to the present invention directs the sample radiation of at least two samples during time periods which at least partially overlap towards said detection device. Thus, sample radiation of different wavelengths can be directed simultaneously by said one auxiliary device.

The auxiliary device preferably is a mirror section consisting of at least one mirror segment, each providing at least one mirror element, which at least intermittently is associated to at least one radiation element. The mirror section transmits at least a part of the radiation of a radiation element while it reflects at least a part of the sample radiation. In the case that the sample radiation is fluorescent light, a mirror element preferably is a dichroic mirror, which is adapted to transmit the excitation light of a certain type of radiation element and to reflect the fluorescence light of the fluorescence marker in the sample. A mirror element is preferably a substantially plane component which is at least intermittently aligned under an 45° angle respective to the normal of the sample holder member.

Preferably, one mirror element is at least intermittently, i.e. for example during a scanning step, associated to a certain radiation element within the radiation device. Preferably, one mirror element is permanently assigned to a radiation element which allows to fix the geometrical arrangement of a mirror element respective to its assigned radiation element to an optimal position. The arrangement of the mirror elements within a mirror segment and the arrangement of the mirror segments within the radiation device is substantially dependent on the arrangement of the radiation elements which are associated to the respective mirror elements. Thus, it is for example possible and preferred that a mirror segment contains at least one row of mirror elements which are assigned to at least one row of radiation elements respectively, in particular to a row of radiation elements with a row-emission frequency.

The mirror section is preferably at least partially connected to the radiation device. Thus, the position of the mirror section is at least partially fixed to the radiation device which helps to avoid errors in aligning the radiation path. In a preferred embodiment of the present invention, the mirror section is allocated and fixed as a whole respective to the radiation device whereby the need to position the mirror section during the measurement is eliminated.

Further possible and preferred, the mirror section is at least partially arranged movable respective to the radiation device. This allows to deallocate the space which was allocated to the mirror segment and allows for example to allocate said space to another radiation path. Moreover it is preferred that at least one mirror segment or at least one mirror element is mounted pivoting respective to the radiation device. In this case it is further preferred that motion means like a step motor, a piezo actuator or a magnetic switch are provided which can apply a force to the mirror segment or mirror element to move it. In particular said motion means are able to pivot a mirror segment or element from a first position in which the mirror segment or element is allocated to a second position in which the mirror segment or element is deallocated.

Preferably, the mirror elements are formed one-piece from a substrate, in particular a substrate made from glass or plastic, for example formed by the segmental coating of one glass substrate. Alternatively and preferred, the mirror section is formed by at least one or several mirror segments wherein a mirror segment is a one-piece device which provides several mirror elements. The mirror segments preferably are connected by at least one connection means which for example is a frame construction, an encasing transparent matrix or a plastic or cement-like material. In contrast it is also possible and preferred, that the mirror segments are substantially separate devices. In another preferred design of the mirror section, the mirror elements may be further split up into mirror-subelements which may be one-piece or separate pieces.

The auxiliary device is preferably arranged substantially in parallel to the radiation device and the sample holder member and preferably arranged substantially between the sample holder member and the radiation device. Alternatively and preferred, the mirror section is arranged such that the sample holder member is substantially positioned between the mirror section and the radiation device.

The first optical path is preferably defined such that the radiation, originating in the radiation source, exits the emitter element of a radiation element, transmits the auxiliary device, enters the area of a sample where it causes a sample radiation. The sample radiation leaves the sample area via a second optical path towards the auxiliary device where the sample radiation is directed via said second optical path towards the detector device.

The auxiliary device preferably provides optical means to manipulate the radiation along the radiation path like fibers, filters, lenses, apertures and the like. Such optical means might in particular assist in choosing the appropriate excitation frequency, collimating the radiation, direct the radiation, focusing the radiation on the sample, and/or reducing stray light etc.

Alternatively and preferred, the auxiliary device comprises optical fibres which are connected to the radiation device and the detection device. A first optical fibre connects optically one radiation element with one at least intermittently associated sample, thus employing the first part of the radiation path. The second part of the radiation path comprises a second optical fibre which leads the sample radiation which is collected near the sample toward the detection device.

Preferably the apparatus provides at least one optical block device. Said optical block device preferably comprises at least in part the components of said radiation device, preferably comprises said radiation device and preferably comprises said auxiliary device. Preferably, said optical block device forms a module of said apparatus, which is capable of being exchanged with other optical block devices. Thus, it is possible to use the same apparatus with different optical block devices. This offers the advantage that the apparatus can be easier used with different geometrical arrangements of sample containers, e.g. using both, 96- and 384-well plates and other sample holder arrangements.

It is further possible and preferred that the apparatus comprises only one or a plurality of optical block devices, which may change position. This change of position can be in dependence on the geometrical arrangements of sample containers, which is desired by the user of the apparatus. The change of position is preferably performed automatically, e.g. upon initiation of a computer program, or may be initiated by the user. Preferably the apparatus provides change positioning means in order to perform said change of position. Said change positioning means preferably are adapted to move said at least one optical block relative to the sample positions. Preferably said change positioning means comprises at least one translation positioning means which is capable to perform a translation motion of said at least one optical block device. Further, said change positioning means preferably comprises at least one rotation positioning means which is capable to perform a rotation motion of said at least one optical block device. The axis of rotation can be vertically and/or horizontally and/or be aligned in other directions.

Further preferred, said change positioning means is adapted to perform both, translation and rotation motions. Said change positioning means can comprise for example a spindle drive, and/or a linear motor, and/or electronic motors or actuators, and/or pneumatic or electrochemical drives or actuators or the like. Using several optical block devices in one apparatus, which are exchangeable, offers the advantage that the optical components may be encapsulated by a housing in order to prevent dirt from polluting the optical pathways. Further, it can be avoided that optical blocks have to be exchanged manually, thus avoiding mechanical stress by user manipulation.

The sample holder member preferably provides a container position array which is an array of positions which are adapted to hold or fix a receptacle which can contain a sample, wherein the sample can comprise at least one source of sample radiation, e.g. a fluorescence marker. The geometry of the container position array preferably corresponds at least partially to the geometry of an array of radiation elements of the radiation device. In particular, the sample holder member can comprise the thermoblock of a thermocycler which can be used for PCR. The thermoblock is made of metal, e.g. aluminum, silver or copper, and can comprise said container position array. The container position array can be formed to hold a titration plate (MTP) or individual receptacles. The temperature of the thermoblock is preferably adjusted by one or more heating elements like thermoelectric coolers (peltier-elements). Further possible and preferred configurations of the sample holder member comprising positioning means for samples are described by U.S. Pat. No. 6,852,986 B1 which is incorporated herein by reference. Preferably, the apparatus, in particular the radiation device and the controller device, is adapted such that all samples contained in a sample holder member with a total number of x times y sample positions can be irradiated by radiation during time periods which at least partially overlap.

The at least one detection device of the apparatus according to the present invention detects the sample radiation of at least two samples as a sum during time periods which at least partially overlap. The detection device is preferably fitted with an optical device that can reproduce the sample radiation of at least two samples as a sum during time periods which at least partially overlap onto at least one light sensitive detector unit. It is one advantage of the apparatus according to the present invention that the number of detector units can be reduced down to one detector unit. This may reduce the costs and the maintenance requirements of the detection device and thus, the costs of the apparatus according to the present invention, in particular in contrast to the prior art detection devices that use one detector unit for each emitter element. However, it is possible that a plurality of detector devices are used which might in particular be optimized for the detection of sample radiations of different spectral ranges. It is further possible and preferred, that the at least one detector device is firmly attached to the radiation device. By using such a configuration, the length of the second optical path is kept constant during the measurement, e.g. during the screening of an MTP, which enhances the comparability and reliability of the data.

Said optical device preferably comprises an array of optical fibres that serves as a collimator. Alternatively and preferred the optical device comprises one or more lens elements that collimate the sample radiation to transmit it towards said at least one detector unit. The optical device further preferably comprises at least one additional optical means to manipulate the radiation along the radiation paths and to optimize the radiation for being detected by the at least one detector unit wherein said optical means is taken from the group of optical means which comprises fibers, filters, lenses, mirrors, apertures and the like.

Preferably the detection device comprises one detector unit. The preferred use of providing only one detector unit or at least few detection units further offers the advantage that the costs and the maintenance requirements of the detection device and thus, the apparatus are minimized. Further, the reliability of the apparatus is enhanced because the error involved in the operation of more than one detector unit is reduced. Such an error can for example be due to different or changing operating states of different detector units or due to temperature variations between the detector units.

It is possible and preferred that more than one detector units are provided. Preferably the sample radiation of several samples is bundled and directed to different detector units. Thus it is possible to improve the S/N of the sample radiation which is discriminated within said sum of sample radiations by means of the evaluation device and assigned to the radiation element which caused said sample radiation. It is further possible and preferred that the sum of sample radiations or at least one of said bundles of sample radiations is split into parts for instance by prisms, diffraction gratings and the like, to transmit the selected parts towards an individual detector unit. This allows for example to differentiate the detected radiation in terms of frequency and to optimize the evaluation efficiency of the detected sample radiation which in turn assists to improve said S/N.

A detector unit preferably is selected from a group of devices including photodiodes, avalanche photodiodes, phototransistors, photoconductive detectors, linear sensor arrays, CCD detectors, CMOS optical detectors, CMOS array detectors, photomultipliers, photomultiplier arrays, direct image sensors or other devices that can measure at least one property of the sample radiation and output the result of the measurement as an electrical signal.

The apparatus according to the present invention comprises a control device, which preferably individually controls said at least one radiation element. Preferably, the control device is adapted to provide modulation signals wherein each modulation signal is used to modulate the radiation which is emitted by an emitter element. However, a separate modulation device can be provided which generates the modulation signals, while the activity of the emitter elements is controlled by the control device. Said modulation device can be physically separated from—but can be connected to—the control device and/or the radiation device. Moreover, said modulation device can be a module of the control device or another device of the apparatus, e.g. the evaluation device. It is possible and preferred that the control device or said modulation device generates the modulation signals. Moreover, it is possible and preferred that the control device or said modulation device use modulation signals which are supported by an operational software of the apparatus or a data memory of the apparatus. Respectively preferred, the control device comprises at least one data processing unit (CPU), in particular a field programmable gate array (FPGA) device or a microprocessor/microcontroller, at least one type of data memory, and a power supply unit which supplies the control device with at least one supply voltage. Said microcontroller of the evaluation device is preferably connected to the control device. The control device preferably is adapted to communicate with the radiation device and the evaluation device. Preferably, the control device comprises an oscillator device, e.g. comprising a common crystal oscillator, which provides a mother clock timing to synchronize the operations of the radiation device and the evaluation device.

Preferably, the control device is adapted to let a number of emitter elements emit radiation during time periods which at least partially overlap, and to cause a number of sample radiations to be emitted from the samples during time periods which at least partially overlap and to be detected during time periods which at least partially overlap by the detection device as a sum signal. Said number is preferably chosen from a group of numbers comprising 2, 3, 4, 6, 8, 10, 12, 14, 16, 24, 32. The choice of said number from said range of numbers offers the advantage that a more effective evaluation of the sample radiation from said sum signal can be performed, compared to an embodiment with a much higher number, e.g. 96 or 384. This means in particular that the S/N of the sample radiations at a given overall measurement time is improved or that for a given S/N the overall measurement time is reduced. Using said lower number leads to a reduction of the errors which are involved with the limited bandwith of the used signals and computing effort required for the transformation operations, e.g. the digitalisation or a fourier transformation, which are related to the evaluation of the measured signals.

An improved S/N allows in particular to monitor the progress of a PCR in the very beginning of the PCR when the concentration of functional fluorescent markers in the sample is yet low. Further, the improved sensitivity of the apparatus and the method according to the present invention allows a high throughput for systems which are working 24 h in automated lab environments.

The apparatus according to the present invention further comprises an evaluation device which is adapted to evaluate the sample radiation of at least one individual sample from said sum signal. Preferably, the evaluation device is a modular computing device which is specialized in substantially only evaluating the measured data. Such a modular concept offers the advantage of improved data control compared to any prior art apparatus with only one single data processing unit. A part of the functions of the evaluation device preferably is performed by devices which are modules of the evaluation device or, alternatively and preferred, separated from—but interacting with—the evaluation device. The evaluation device preferably comprises a transformation device which is capable of performing a transformation operation on said sum signal to evaluate the sample radiation of at least one individual sample from said sum signal. Said transformation operation is preferably a mathematical operation, in particular a fourier transformation. Further, the evaluation device preferably comprises a decoding device for performing a decoding operation on said sum signal to evaluate the sample radiation of at least one individual sample from said sum signal. The decoding operation preferably comprises a step of multiplying the sum signal with a modulation signal. The evaluation device can be connected to the control device or any other device, e.g. said modulation device or an additional computing device or can be connected or is connectable to at least one data input/output device.

The evaluation device preferably comprises noise reduction means and, respectively preferred, comprises a bandpass filter, a digital highpass filter, a transimpedance amplifier, which preferably has a highpass function, a sampling device for sampling the sum signal, an analogue to digital converter, a central processing unit which preferably is a field programmable gate array (FPGA), an oscillator device, e.g. comprising a crystal oscillator, at least one type of data memory and/or a microcontroller which preferably is connected to the control device. Further, the evaluation device preferably comprises an averaging device, which is capable of averaging the sum signal, preferably after at least one step of pre-processing of the sum signal.

Said transformation device, said decoding device and said averaging device can be physically separated and can further be connected for interaction with the evaluation device, for performing their specific function on the data which are provided to them by the evaluation device. Moreover, the evaluation device and the control device can be at least partially built integrally as an integrated device which allows for a compact design of the apparatus, thus reducing costs.

The skilled person will appreciate that the features of the apparatus according to the preferred embodiment, which is described in the following, can be extracted and combined with other features according to the present invention to further modify the apparatus and method according to the present invention. Further, additional features may be added to the apparatus according to the preferred embodiment.

In a possible and preferred embodiment of the apparatus according to the present invention, the apparatus is adapted such that all samples contained in a sample holder member with a total number of x times y sample positions can be irradiated by radiation during time periods which at least partially overlap. Preferably, at least a part of the radiation device and the sample holder member are adapted to be moved against each other during the investigation procedure, which preferably comprises the investigation of all $x*y$ samples. Preferably, the array of radiation elements consists of r rows and c columns wherein the radiation elements of each row show the same row-emission spectrum, i.e. colour, which is one out of n different emission spectra and wherein further m blocks of rows are provided, wherein a number of preferably at least m−1 blocks have the same sequence of rows with row-emission spectra (r, c, n and m are natural numbers) and preferably one block has said sequence in part. Preferably, $r=x+n-1$ and preferably $r=(n*m)-1$. This way, the array of radiation elements is preferably structured into a pattern comprising m blocks with rows of different colour, wherein m−1 blocks comprise a number of n rows and one block comprises a different number of rows which may be different. Further, the radiation device preferably provides a number of radiation elements which is the same as the number of sample positions of the sample holder member, plus additional n−1 rows of radiation elements. This way, the number of positioning steps of the radiation device relative to the sample holder member is n−1, once the radiation device is positioned in its first position, in order to perform a complete scan of the samples by each type of radiation element.

The apparatus, in particular the radiation device and/or the controller device, is adapted such that the sample radiations from all samples are distinguishable from each other by utilizing multiplex technique, e.g. by implementing at least one of FDMA, CDMA, TDMA, WDMA or phase multiplexing methods. For the preferred embodiment of the apparatus, the radiation of a row of radiation elements within said array of radiation elements is preferably modulated by a modulation technique. Preferably, each row of the same row-emission spectrum, i.e. the same colour, emits radiation with a different modulation. The modulated radiation of each emitter/radiation element excites a sample radiation, which show a respectively corresponding modulation. Thus it is possible to distinguish between sample radiation of the same colour, which is in particular received simultaneously by a detector unit. In particular, it is possible to activate rows of radiation elements with the same colour and to evaluate the corresponding sample radiations during time periods which at least partially overlap. Said modulation technique is preferably a code multiplex technique, which in particular uses Hadamard-code or pseudo noise code or the like. It is further possible and preferred that said modulation technique is a frequency multiplex technique, which in particular uses different modulation frequencies.

Preferably, a number of r, in particular $r=x+(n-1)$ input ports are provided with the apparatus and/or the radiation device, wherein each input port is adapted to receive the radiation, which is to be transmitted towards a number of $c=y$ radiation elements, which in consequence show the same row-emission spectrum. However it is possible and preferred that a number of $r=c$ input ports are provided, wherein in this case the number of output ports is preferably $x+n-1$. Preferably, each row of an array of radiation elements is assigned to an input port and receives from a radiation source a radiation, which is in particular modulated. Preferably, a plurality of radiation elements, in particular a plurality of rows, are activated at least partially simultaneously. Preferably, a number of $x*y$ radiation elements, in particular a number of y rows of radiation elements, are activated at least partially simultaneously. Preferably, all sample positions of the sample holder member are irradiated at least partially simultaneously. This offers the advantage of a highly parallel measuring and a fast obtaining of data. In particular with the low number of only n−1 positioning steps, which are required to measure each sample under each radiation colour, the speed of completely measuring e.g. all samples of a microtiter plate is improved. The use of input ports reduces the number of radiation sources which are required and on the other hand offers the advantage to simultaneously transfer the same type of radiation to a plurality of radiation elements or emitter elements.

Further, preferably at least one output port is provided, wherein said output port is adapted to output the sample radiation, which is received from a plurality of samples during time periods which at least partially overlap and which is to be transmitted towards at least one detection device. Preferably, a number of $c=y$ output ports are provided, wherein each of said output ports is adapted to output the sample radiation, which is received from a number $x=r-(n-1)$ of samples during time periods which at least partially overlap and which is to be transmitted towards at least one detection device, wherein each of said detection devices generates a sum signal. Preferably, the apparatus provides at least one output port, which is assigned to the radiation and sample radiation, which corresponds to one column of radiation elements of said array of radiation elements.

Preferably, the distribution of sample radiation from the samples to the output ports is at least partially realized by fiber optics. In particular, the sample radiation of each sample is preferably directed towards one of a number of $x*y$ lenses, which collect each sample radiation and direct it to the input end face of at least one optical fiber.

It is further possible and preferred that the distribution of sample radiation from the samples to the output ports is at least partially realized by integrated optics, e.g. based on inorganic or organic transparent materials, e.g. polydimethylsiloxane (PDMS). By using such substrate-based optical signal transport means, the volume of radiation path means is reduced. Therefore a more compact design of a radiation device or apparatus is possible.

Preferably, the apparatus comprises a number of s beam splitter means, in particular dichroic mirrors or prisms, which are in particular arranged downstream to the output ports, wherein s>0. However, it is also possible and preferred that no beam splitter means are used. Preferably said sample radiation, which is output from an output port, is split into different spectral components by a number of beam splitter means, wherein each spectral component is transmitted towards a detection unit, which generates a sum signal. Preferably, a number of s beam splitter means is used to generate preferably a number of s+1 different spectral components. It is further possible and preferred that the sample radiation, which is output from an output port, is filtered by a filter wheel, which comprises a number of n filters, wherein by each filter a different spectral component is filtered and transmitted towards a detection unit, which generates a sum signal. Said sum signal is preferably decoded by demodulation. Preferably, the evaluation device is adapted to evaluate the sample radiation of each individual sample from a number of sum signals, which each corresponds to the sample radiations from a different output port. The combination of a spectral decomposition and a multiplex method, in particular a code multiplex method, improves the efficiency of utilizing the dynamic range of the detector units.

Using the explanations and definitions of the description of the present invention, the following embodiments of the apparatus according to the present invention are provided:

The apparatus according to the present invention wherein a minimum of two emitter elements provide radiation with different radiation spectra.

The apparatus according to the present invention wherein at least a part of the radiation device and the sample holder member are adapted to be moved against each other during the investigation procedure.

The apparatus according to the present invention wherein it comprises at least two radiation elements wherein each radiation element comprises one emitter element which is at least intermittently assigned to one sample.

The apparatus according to the present invention wherein it comprises a plurality of radiation elements which are arranged in an array.

The apparatus according to the present invention wherein said array provides a pattern on the basis of at least two radiation elements with different radiation spectra, i.e. said at least two radiation elements are adapted to provide at least two emitter elements which provide radiation with different radiation spectra.

The apparatus according to the present invention wherein the radiation elements are arranged in an array of r rows and c columns (r and c are natural numbers).

The apparatus according to the present invention wherein the radiation elements of each row are arranged in a row-dependent sequence of at least one emission spectrum.

The apparatus according to the present invention wherein the array consists of r=n*m rows and c columns wherein the radiation elements of each row show the same row-emission spectrum which is one out of n different emission spectra and wherein further m blocks of rows are provided, each block having the same sequence of rows with row-emission spectra (r, c, n and m are natural numbers).

The apparatus according to the present invention wherein the array consists of r=(n*m)−1 rows and c columns wherein the radiation elements of each row show the same row-emission spectrum which is one out of n different emission spectra and wherein further m blocks of rows are provided, wherein m−1 blocks have the same sequence of rows with row-emission spectra (r, c, n and m are natural numbers) and one block has said sequence in part.

The apparatus according to the present invention wherein the array consists of r=n*m rows and c columns wherein a plurality of blocks with m rows each are provided, wherein the radiation elements of each block show the same block-emission spectrum which is one out of n different emission spectra (r, c, n and m are natural numbers).

The apparatus according to the present invention wherein the number of radiation elements exceeds the number of sample positions.

The apparatus according to the present invention wherein the number of radiation elements exceeds the number of sample positions by n*c.

The apparatus according to the present invention wherein the emitter elements are LEDs, or SMD-LEDs, high-power LEDs, OLEDs, laser diodes or combinations thereof.

The apparatus according to the present invention wherein at least one emitter element comprises the end face of an optical fiber which is adapted to emit radiation.

The apparatus according to the present invention wherein the radiation, emitted by said at least one radiation element, said at least one emitter element and said at least one sample, is light.

The apparatus according to the present invention wherein the radiation emitted by said at least one radiation element and said at least one emitter element is white light.

The apparatus according to the present invention wherein it comprises locking means which are adapted to preserve predefined positions of at least a part of the radiation device in relation to the sample holder member.

The apparatus according to the present invention wherein the radiation device comprises at least one substrate on which the plurality of radiation elements is mounted.

The apparatus according to the present invention wherein the radiation device comprises a support member which supports said at least one substrate.

The apparatus according to the present invention wherein said substrate is movable against said support member.

The apparatus according to the present invention wherein said substrates are rotatable around an axis of rotation.

The apparatus according to the present invention wherein the axis of rotation is aligned substantially in parallel to the sample holder member.

The apparatus according to the present invention wherein the axis of rotation is aligned substantially perpendicular to the sample holder member.

The apparatus according to the present invention wherein the radiation device comprises at least one cooler.

The apparatus according to the present invention wherein the radiation device comprises at least one temperature sensor.

The apparatus according to the present invention wherein the radiation device comprises at least one controller to control at least one electric device of the radiation device.

The apparatus according to the present invention wherein the control device is a part of said radiation device.

The apparatus according to the present invention wherein the control device is a part of said evaluation device.

The apparatus according to the present invention wherein the control device is an individual device.

The apparatus according to the present invention wherein the radiation device comprises a lens array which provides a number of lenses wherein an individual lens is capable to direct the radiation of a radiation element.

The apparatus according to the present invention wherein the radiation device comprises a lens array which provides a number of lenses wherein an individual lens is capable to direct the radiation of an emitter element.

The apparatus according to the present invention wherein the substrate which carries the radiation elements is movable against the lens array.

The apparatus according to the present invention wherein the number of lenses of the lens array equals the overall number of radiation elements of the radiation device.

The apparatus according to the present invention wherein the number of lenses of the lens array equals the overall number of emitter elements of the radiation device.

The apparatus according to the present invention wherein the number of lenses of the lens array equals the overall number of the sample positions of the sample holder member.

The apparatus according to the present invention wherein the radiation device comprises a plurality of apertures which are adapted to transmit radiation.

The apparatus according to the present invention wherein the radiation device comprises at least one reference emitter element.

The apparatus according to the present invention wherein it comprises an auxiliary device which is adapted to direct the sample radiation of at least two samples during time periods which at least partially overlap towards at least one detection device.

The apparatus according to the present invention wherein the auxiliary device is a mirror section with at least one mirror segment, each providing at least one mirror element, which is associated to at least one radiation element.

The apparatus according to the present invention wherein said mirror section is arranged substantially in parallel to the radiation device and the sample holder member, and that said mirror section transmits at least part of the radiation of a radiation element while it reflects at least part of the sample radiation.

The apparatus according to the present invention wherein at least one mirror segment of the mirror section is firmly attached to the radiation device.

The apparatus according to the present invention wherein at least one mirror segment of the mirror section is movably attached to the radiation device.

The apparatus according to the present invention wherein at least one mirror segment of the mirror section is pivoted to the radiation device.

The apparatus according to the present invention wherein the mirror section provides one mirror segment with r rows wherein each row has at least one mirror element arranged in a row-dependent sequence which is dependent on the sequence of corresponding radiation elements.

The apparatus according to the present invention wherein the mirror section provides one mirror segment with r mirror elements which are defined in dependence on the corresponding radiation elements.

The apparatus according to the present invention wherein the mirror section is arranged substantially between the sample holder member and the radiation device.

The apparatus according to the present invention wherein the sample holder member is arranged substantially between the mirror section and the radiation device.

The apparatus according to the present invention wherein the sample holder member comprises a thermoblock.

The apparatus according to the present invention wherein the sample holder member comprises at least a part of a thermocycler which is adapted to be used in PCR related operations.

The apparatus according to the present invention wherein the sample holder member is adapted to hold single standard PCR receptacles which are capable of supporting a sample.

The apparatus according to the present invention wherein the sample holder member is adapted to hold a standard PCR plate which provides a plurality of receptacles which are capable of supporting a sample.

The apparatus according to the present invention wherein the sample holder member comprises a plastic sheet which covers the openings of the receptacles.

The apparatus according to the present invention wherein the sample holder member comprises a lid to close the receptacles.

The apparatus according to the present invention wherein the lid has a plurality of apertures wherein each aperture corresponds to a sample position.

The apparatus according to the present invention wherein an aperture of the lid is shaped like a hollow-cylinder.

The apparatus according to the present invention wherein the lid is contacted by heating elements and wherein the temperature of the lid is controllable.

The apparatus according to the present invention wherein the sample holder member comprises an array of lenses.

The apparatus according to the present invention wherein the lid comprises a plurality of lenses which are arranged at said apertures of the lid.

The apparatus according to the present invention wherein the sample contains at least one fluorescent marker which is capable to be caused to emit a sample radiation upon irradiation.

The apparatus according to the present invention wherein the sample contains PCR reagents.

The apparatus according to the present invention wherein the sample contains a reagent from the group of reagents which comprises triphenylmethane dyes, rhodamine dyes, cyanine dyes, intercalating dyes (e.g. ethidium salts, Sybr Green), FRET-probes and fluorescent nanoparticles.

The apparatus according to the present invention wherein the detection device comprises at least one detector detection unit.

The apparatus according to the present invention wherein the detection unit is selected from a group of detection units which comprises photodiodes, avalanche photodiodes, phototransistors, photoconductive detectors, linear sensor arrays, CCD detectors, CMOS optical detectors, CMOS array detectors, direct image sensors, photomultipliers and photomultiplier arrays.

The apparatus according to the present invention wherein the detection device comprises an optical device that receives the sample radiation of at least on sample and directs said light toward at least one detection unit.

The apparatus according to the present invention wherein said optical device of the detection device comprises an arrangement of optical fibers of which the light entry surfaces are end faces which are mutually spaced and parallel and the light exit surfaces are end faces which are mutually parallel and adjacent.

The apparatus according to the present invention wherein the detection device comprises a lens array.

The apparatus according to the present invention wherein the detection device comprises optical means which are selected from prisms, lenses, beamsplitters, grids, filters and interference filters.

The apparatus according to the present invention wherein the evaluation device comprises a transformation device which is capable of performing a transformation operation on said sum signal to evaluate the sample radiation of at least one individual sample from said sum signal.

The apparatus according to the present invention wherein the transformation operation is a mathematical operation.

The apparatus according to the present invention wherein the transformation operation is a fourier transformation, correlation or any other adequate operations.

The apparatus according to the present invention wherein the evaluation device comprises a decoding device for performing a decoding operation on said sum signal to evaluate the sample radiation of at least one individual sample from said sum signal.

The apparatus according to the present invention wherein the evaluation device comprises noise reduction means.

The apparatus according to the present invention wherein the noise reduction means of the evaluation device comprise a bandpass filter.

The apparatus according to the present invention wherein the noise reduction means of the evaluation device comprise a digital highpass filter.

The apparatus according to the present invention wherein the evaluation device comprises a transimpedance amplifier.

The apparatus according to the present invention wherein the transimpedance amplifier has a highpass function or a bandpass function.

The apparatus according to the present invention wherein the evaluation device comprises a sampling device for sampling a signal.

The apparatus according to the present invention wherein the evaluation device comprises an analogue to digital converter.

The apparatus according to the present invention wherein the evaluation device comprises a central processing unit and an oscillator device.

The apparatus according to the present invention wherein the central processing unit of the evaluation device is a field programmable gate array (FPGA).

The apparatus according to the present invention wherein the evaluation device comprises at least one type of data memory.

The apparatus according to the present invention wherein the evaluation device comprises a microcontroller.

The apparatus according to the present invention wherein the microcontroller of the evaluation device is connected to the control device.

The apparatus according to the present invention wherein the evaluation device is connected to the detection device and the control device.

The apparatus according to the present invention wherein a plurality of emitter elements are emitting light during time periods which at least partially overlap, causing a plurality of sample radiations to be emitted from the samples during time periods which at least partially overlap and to be detected during time periods which at least partially overlap by the detection device as a sum signal.

The apparatus according to the present invention wherein the control device is connected to the radiation device to control the activity of the radiation elements.

The apparatus according to the present invention wherein the control device comprises a central processing unit and an oscillator.

The apparatus according to the present invention wherein the central processing unit of the control device is a field programmable gate array (FPGA).

The apparatus according to the present invention wherein the control device comprises a trigger device to start processes.

The apparatus according to the present invention wherein the control device comprises at least one type of data memory.

The apparatus according to the present invention wherein the control device is adapted to modulate the radiation which is emitted by a radiation element with a modulation signal.

The apparatus according to the present invention wherein the control device is adapted to modulate the radiation which is emitted by each of said at least two emitter elements with an individual modulation signal.

The apparatus according to the present invention wherein the control device is adapted to modulate the radiation which is emitted by each emitter element with an individual modulation signal.

The apparatus according to the present invention wherein the evaluation device is adapted to receive said individual modulation signals as specific reference signals to evaluate the sample radiation of at least one individual sample from said sum signal.

The apparatus according to the present invention wherein the control device is adapted to use modulation signals, which are generated according to a frequency division multiple access (FDMA) method, to modulate the radiation of said at least two emitter elements during time periods which at least partially overlap.

The apparatus according to the present invention wherein the modulation signal of each of said at least two emitter elements is individual.

The apparatus according to the present invention wherein the individual modulation frequencies are determined such that one modulation frequency is not the harmonic of any other modulation frequency and that the distance of the modulation frequencies is larger than the bandwidth of the spectral line which is determined by a fast fourier transformation of the modulation signal.

The apparatus according to the present invention wherein the modulation frequencies (MF) are chosen from within the range of 100 Hz≦MF≦100 MHz, preferably from 1 kHz≦MF≦1 MHz and preferably from 100 kHz<MF<123 kHz.

The apparatus according to the present invention wherein the control device is adapted to use a spread-spectrum code to generate the modulation signals.

The apparatus according to the present invention wherein the control device is adapted to use modulation signals, which are generated according to a code division multiple access (CDMA) method, to modulate the radiation of said at least two emitter elements during time periods which at least partially overlap.

The apparatus according to the present invention wherein the modulation signals of said at least two emitter elements are generated using at least one sequence of at least one pseudorandom number code.

The apparatus according to the present invention wherein the control device is adapted to use modulation signals by applying the same pseudorandom number code to a plurality of emitter elements, which are emitting during time periods which at least partially overlap, wherein the pseudorandom number code of an individual emitter element is shifted about at least one bit against the pseudorandom number codes of the other emitter elements.

The apparatus according to the present invention wherein the control device is adapted to use modulation signals, which are generated by using orthogonal sequences of Hadamard-code, to modulate the radiation of each of said at least two emitter elements, which are emitting during time periods which at least partially overlap, by a different one of said sequences of Hadamard-code.

The apparatus according to the present invention wherein the control device is adapted to use modulation signals which are generated according to a time division multiple access (TDMA) method to modulate the radiation of said at least two emitter elements during time periods which at least partially overlap.

The apparatus according to the present invention wherein the control device is adapted to use modulation signals which are generated according to a wavelength division multiple access (WDMA) method to modulate the radiation of said at least two emitter elements during time periods which at least partially overlap.

The apparatus according to the present invention wherein the control device is adapted to use modulation signals which are generated according to a combination of the FDMA, CDMA, or TDMA, WDMA or phase modulation methods to modulate the radiation of at least two emitter elements during time periods which at least partially overlap.

The apparatus according to the present invention wherein the modulation signals are square (wave) signals or rectangular signals.

The apparatus according to the present invention wherein the modulation signals are sinusoidal, triangular, saw tooth or impulses.

The apparatus according to the present invention wherein at least two of the square signals are phase shifted.

The apparatus according to the present invention wherein the transformation means is adapted to transform the sum signal in order to determine the quantity of an individual sample radiation from said sum signal wherein said quantity is the value which quantifies a property of said sample radiation.

The apparatus according to the present invention wherein the control device is adapted to adjust the time period of irradiation of a sample by an radiation emitter element in dependency on the quantity of the detected sample radiation.

The apparatus according to the present invention wherein the evaluation device comprises a correlator device which is adapted to correlate a modulation signal with the sum signal.

The apparatus according to the present invention wherein the evaluation device comprises a multiplicator device which is adapted to multiply a modulation signal with the sum signal.

The apparatus according to the present invention wherein the evaluation device and the control device are at least partially built integrally as an integrated device.

The overall measurement time is in particular determined by the number of motion steps which are performed by the radiation device relative to the sample holder member. Said motion involves stopping the accelerated device which leads to mechanical oscillations (vibrations) of the moved device. Since the oscillations would interfere with a reproducible measurement, a decay time (settling time) has to pass wherein the oscillations are damped such that a measurement is possible. Thus, the overall measurement time is at least determined by the time of motion, the decay time, the time of measurement during one step, all multiplied by the number of motion steps. According to the present invention, the overall measurement time is preferably 5 seconds and lower for a sample plate with 96 samples, and is preferably about 1 s. The decay time is preferably 300 ms and lower, and is preferably 100 ms. Thus, a fast quantitative measurement is achieved which in particular allows a precise monitoring and control of a PCR process.

Other preferred features and advantages of the apparatus according to the present invention can be taken from the following description of methods according to the present invention, in particular those methods of operating the apparatus according to the present invention.

According to one embodiment, a method for radiometrically investigating a plurality of samples, comprises the steps:

controlling a radiation device by means of a control device wherein said radiation device provides at least one radiation element and at least two emitter elements, wherein each radiation element comprises at least one emitter element, let said at least two emitter elements emit radiation during time periods which at least partially overlap, providing a sample holder member which provides a plurality of sample positions for supporting a plurality of samples, controlling the relative position of the radiation device and the sample holder member which are at least partially adapted to be moved against each other during the investigation procedure, irradiating a different sample by the radiation of said at least two emitter elements via a first optical path to cause the sample to emit sample radiation with at least one sample radiation frequency via a second optical path towards at least one detection device, detecting the sample radiation, which is emitted by at least two samples during time periods which at least partially overlap, as a sum signal by said at least one detection device, evaluating the sample radiation of at least one individual sample from said sum signal by an evaluation device.

According to a further embodiment, a method for radiometrically investigating a plurality of samples, comprises the steps:

controlling a radiation device by means of a control device wherein said radiation device provides at least one radiation element and at least two emitter elements, wherein each radiation element comprises at least one emitter element, wherein a minimum of two emitter elements provide radiation with different radiation spectra, let said at least two emitter elements emit radiation during time periods which at least partially overlap, providing a sample holder member which provides a plurality of sample positions for supporting a plurality of samples, irradiating a different sample by the radiation of said at least two emitter elements via a first optical path to cause the sample to emit sample radiation with at least one sample radiation frequency via a second optical path towards at least one detection device, detecting the sample radiation, which is emitted by at least two samples during time periods which at least partially overlap, as a sum signal by said at least one detection device, evaluating the sample radiation of at least one individual sample from said sum signal by an evaluation device.

Preferably, said methods are applied by using the apparatus according to the invention. Said methods according to the present invention offer the particular advantage that in contrast to a sequential operation of detection of at least two sample radiations, the at least partial parallel measurement of at least two different sample radiations offers the possibility to reduce the overall detection time of said at least two sample radiations which means that the overall measuring time can be reduced. Moreover, by detecting the sample radiation of at least two samples as a sum signal during time periods which at least partially overlap, i.e. by an at least partially simultaneous detection of sample radiations, it is possible to reduce—if desired—the steps of motion of the radiation device relative to the sample holder member.

Said parallel measuring of at least two different sample radiations in a sum signal requires that a method is provided which allows to recover the individual signal which refers to a specific sample radiation from said sum signal. According to the present invention, several addressing methods are appropriate to address each of a plurality of samples, to measure their signal-answer as a sum signal and to resolve the fraction of the sum signal that refers to the specific sample radiation which was addressed. The addressing methods preferably are used in combination or without combination with one of the other addressing methods.

Relating to the case of fluorescence applications, a sample might contain more than one fluorescence marker. Each fluorescence marker is capable to emit fluorescence light of a specific emission spectrum which might be separated by the fluorescence light of the other fluorescence markers in the sample, in particular by using conventional fluorescence optics, i.e. filters, beamsplitters, mirrors and the like. As an alternative to conventional optics, other devices might be used which are capable to distinguish the radiation of different spectral ranges. As an example for said devices, color sensitive-semiconductor devices, e.g. specific direct color-photodiodes or direct color CMOS image sensors, might be used, which are capable of distinguishing and measuring different spectral ranges simultaneously without using filters or prisms to split the incident radiation. Thus, in an addressing method, hereinafter referred to as "color-multiplexing method" or wavelength division multiple access (WDMA) method, it is possible to take use of the different emission spectra of different fluorescence markers, to resolve the sample radiation of a specific fluorescence marker in a sample. It is possible that at least a part of the sample radiations which are measured as a sum signal are caused by fluorescence markers from a single sample, e.g. a solution with fluorescence markers in a receptacle. It is further possible that the sample radiations which are measured as a sum signal are caused by fluorescence markers from more than one sample, in particular that the sample radiations from specific fluorescence markers origin in a different sample (receptacle) each. This is of particular advantage if a plurality of samples have to be measured in a short time, as it is the case in screening methods. Said color-multiplexing method is preferably used in combination with one or more other multiplexing methods, which is described here, and can also be applied to non-fluorescence applications.

On the other hand, in the case of the present invention, the color-multiplexing method is not required to be used if one of the other multiplexing methods—or a combination of them—is used. However, if the color-multiplexing method is not used to resolve a specific sample signal from said sum signal, the use of different radiation spectra is still of advantage. In particular in the case of fluorescence applications, e.g. in PCR methods, it is possible and preferred to use radiation from radiation elements or emitter elements with selected emission spectra which are adapted to efficiently match the excitation spectra of a specific fluorescence markers. In this way, the yield of the sample radiation is increased which results in a decreased measuring time and/or an improved S/N respectively.

According to the present invention, a method preferably uses signal modulation which allows to resolve from a sum signal the specific signal which refers to a specific sample radiation. Accordingly, the evaluation device is preferably adapted to receive individual modulation signals as specific reference signals from the control device to determine, from the sum of the sample radiations that is detected by the detector device, by means of the evaluation device, the individual sample radiation which is emitted by a sample.

It is possible and preferred that a frequency division multiple access (FDMA) method is used to modulate the radiation of at least two emitter elements during time periods which at least partially overlap and to evaluate the sum of sample radiations which is caused by said at least two emitter elements. In the case of FDMA, the radiation of each radiation element and/or emitter element, taken from of a plurality of radiation elements and/or emitter elements, is modulated by a modulation signal which has a selected modulation frequency. The modulation is preferably applied by modulating, e.g. superimposing, the amplitude of the radiation with the modulation signal (amplitude modulation). Possible alternatives to amplitude modulation are the modulation of frequency or phase of the radiation signal. The modulation frequencies are preferably generated by adding a reference frequency to a basic frequency which is referred to as heterodyning method. Preferably, the reference frequency is chosen from a frequency range of 1 kHz to 1 MHz, is preferably chosen from a frequency range of 10 kHz to 500 kHz, is preferably chosen from a frequency range of 50 kHz to 200 kHz and preferably from a frequency range of 80 kHz to 120 kHz, e.g. 100 kHz. Thus, the low frequency range, in particular the range from 0 kHz to 50 kHz, can be gated out. Interference signals, e.g. noise voltages or the 50-Hz noise of power supplies, particularly provide frequencies in said range. Thus, the S/N of the measured signal can be improved by avoiding the low-frequency range. Preferably, the reference frequency is at least one order of magnitude higher than a basic frequency. In the case of reference frequencies in the range of 1 kHz and smaller, an averaging of the measured signal would take too much time. Thus, such a low range of frequencies is preferably avoided for choosing the reference frequency.

According to the present invention, preferably other noise reduction means and methods are provided which assist to improve the S/N of the measured signal. In particular, using the modulation methods according to the present invention offers the advantage of noise reduction because said methods improve the S/N of the measured signal. As a particular advantage of the FDMA method according to the present invention, the measuring of sample radiations from different samples (receptacles) is possible and preferred.

It is possible and preferred that a code division multiple access (CDMA) method is used to modulate the radiation of at least two emitter elements during time periods which at least partially overlap and to evaluate the sum signal of sample radiations which is caused by said at least two emitter elements. According to the present invention, the radiation of each radiation element and/or emitter element, taken from a plurality of radiation elements and/or emitter elements, is modulated by a specific code sequence, which is preferably taken from a set of orthogonal code sequences, e.g. a Hadamard code, a pseudo noise code or other code sequences, in particular code sequences which are used in spread spectrum systems. The modulation is preferably applied using amplitude modulation on a carrier signal, which has a carrier frequency, generating the modulation signal for the CDMA method. The modulation signal is preferably a square wave signal or rectangular signal. The duty cycle of the square signal preferably is smaller than 50% in order to avoid d.c. characteristics of the signal. Channel coding techniques like biphase mark coding, Manchester code, NRZ-code, RZ-code and the like are preferably used to encode the binary modulation code to the carrier signal to generate the modulation signal. This can help to avoid long series of logical ones or zeros without any transitions in the modulation code which makes clock recovery and synchronization easier. In consequence, the signal transfer errors decrease and the S/N of the measured quantity of sample radiation is improved. Moreover, preferably a set of code sequences is achieved by using a single sequence of pseudo-noise code which is preferably applied to the radiations emitted by the radiation elements/emitter elements in a time shifted manner. In this way it is possible to resolve a specific sample radiation, which is caused by the corresponding radiation, from the sum signal by regarding the time-shift of the specific modulation.

It is possible and preferred that a time division multiple access (TDMA) method is used to modulate the radiation of at least two radiation elements during time periods which at least partially overlap and to evaluate the sum of sample radiations which is caused by said at least two radiation elements.

The evaluation of the quantity of a specific sample radiation, e.g. the height of a spectral line and the amplitude of the specific sample radiation, from said sum signal is, according to the present invention, preferably completed by using a transformation device which performs a transformation operation, which preferably is a mathematical operation and/or alternatively at least partially implemented by analogue electronic means. Such a mathematical operation can be a FFT (fast fourier transformation; e.g., a Radix-2 FFT) or an autocorrelation method. In a particular embodiment of the evaluation device according to the present invention, the mathematical operation can be performed by substantially using integer mathematics. This offers the advantage that in a data processing unit, e.g. in an FPGA, only one clock is required to perform one integer calculation. Thus, the calculation of the data is faster and thus, the overall measuring time of the apparatus and the method can be reduced. In a particular embodiment of the data processing unit, no external memory is used to perform the mathematical operation, thus reducing costs. However, the use of external memory units for supporting the data evaluation is possible.

Said quantity can preferably as well be determined by using at least one lock-in amplifier device which monitors the modulation frequency.

The time period of irradiation of a sample by an emitter element preferably is adjusted in dependency on the quantity of the detected sample radiation, to avoid damage of the sample, to reduce the maintenance of the apparatus and to reduce the overall measurement time.

According to one embodiment of the present invention, a method for radiometrically investigating N (N is a natural number with N>1) sample radiations of at least two samples, which are caused by the radiation of N emitter elements of at least one radiation element wherein said N emitter elements are emitting radiation during time periods which at least partially overlap, comprises the steps:
determining a set of N basic frequencies,
adding one reference frequency to each of said basic frequencies wherein said reference frequency is higher than each of said basic frequencies,
using the N sums of the reference frequency and of the basic frequency to provide N modulation signals wherein each modulation signal is used to modulate the radiation of a different emitter element,
detecting the N sample radiations as a sum signal wherein each sample radiation is modulated according to the modulated radiation which caused the respective sample radiation,
demodulating the sum signal by using a demodulation method,
performing a transformation to transfer the demodulated sum signal from a time dependent signal into a frequency dependent signal, and
determining the quantity of at least one individual sample radiation from the amplitude of said frequency dependent signal in dependence on the basic frequency.

Demodulation of the sum signal is performed preferably by a multiplication process, which in particular multiplies the sum signal with the reference frequency. Thus, demodulating the sum signal preferably means a down-mixing of the sum signal. The demodulation is preferably performed by using analogue electronics means, e.g. a ring modulator, and is preferably performed by using digital electronic means.

Said method according to the present invention offers the particular advantage that the radiation signal which is modulated by the modulation signal and a potential interfering signal, which can be in particular a low frequency interference, have a different time characteristics, which reduces the disturbing of the radiation signal by the potential interfering signal. In particular, the frequency band which is used for the modulation, is shifted to higher frequencies compared with the frequencies of potential interference signals. Thus, the interferences are avoided and the S/N of the detected quantity of a sample radiation is improved. Moreover, by using different modulation signals, it is possible to address a specific emitter of sample radiation, e.g. a fluorescence marker, or to address a specific sample of the plurality of samples. By said addressing, the sample radiation of a specific emitter of sample radiation or a specific sample becomes discriminable within the sum of N sample radiations which is detected. In contrast to a sequential operation of detection of N sample radiations, the parallel measuring of N different sample radiations offers the possibility to reduce the overall detection time of said N sample radiations which means that the overall measuring time can be reduced.

Said N basic frequencies are preferably substantially equidistant and are preferably chosen from a frequency range of 0 kHz to 4 kHz. However, it is possible and preferred that said N basic frequencies are not substantially equidistant. Moreover, it is possible and preferred that said N basic frequencies are in the range from 4 KHz to 1 MHz.

The reference frequency is preferably chosen to be much higher than a basic frequency, e.g. to be at least a basic frequency multiplied by the factor 2 or preferably at least a magnitude higher than the basic frequency. A preferred frequency range of the reference frequency is further 80 kHz to 120 kHz Preferably the reference frequency is 100 kHz. However, the reference frequency can be different, as described above.

It is possible and preferred that instead of the frequency division multiple access (FDMA) method at hand, another FDMA method is used to modulate the radiation of at least two radiation elements during time periods which at least partially overlap and to evaluate the sum of sample radiations which is caused by said at least two radiation elements.

The sum signal of N sample radiations which is generated by a detection device is preferably amplified by a transimpedance amplifier. Said transimpedance amplifier is preferably a device which converts a current to a voltage signal. In this case, the sum signal is a current signal, which is converted to a voltage signal by said transimpedance amplifier. Preferably, the transimpedance amplifier has a high-pass function which is capable to suppress low-frequency interferences (noise) of the sum signal at least partially.

The sum signal is preferably filtered by a high-pass filter, in particular a digital high-pass filter. This has the advantage that interfering signals of low frequency are not regarded in the evaluation process and thus, the S/N of the detected quantity of sample radiation is improved.

Said quantity of at least one individual sample radiation from the decoded sum signal preferably is a signal amplitude which is a measure of the strength of the sample radiation which was addressed by said modulation frequency.

Using the explanations and definitions of the description of the present invention, the following embodiments of the method according to the present invention are provided.

In a preferred embodiment, a method according to the present invention for radiometrically investigating a plurality of samples, preferably comprises the steps: irradiating at least partially simultaneously a number of N samples of the entirety of samples, said N samples comprising at least one first group and at least one second group of samples, each group including at least two samples, said first group of samples being irradiated by radiation of a first spectrum, and said second group of samples being irradiated by radiation of a second spectrum, wherein each of said at least one first and one second spectra of an entirety of n spectra are different, wherein each sample within each group of samples is irradiated by radiation of different modulation; and detecting at least partially simultaneously the sample radiation of said N samples.

Preferably the method according to the present invention comprises the steps of: providing an entirety of x*y sample positions or samples, arranged in an array of x rows and y columns, each sample position being adapted to hold a sample; providing an array of radiation elements, which is arrangeable such that each radiation element is at least intermittently assigned to one sample, the array consisting of r=x+n−1 rows (r>=x) and c=y columns wherein the radiation elements of each row show the same row-emission spectrum which is one out of said n different emission spectra and wherein further m blocks of rows are provided, wherein a number (the number >0) of blocks have the same sequence of rows with row-emission spectra (r, c, n and m are natural numbers).

Preferably the method according to the present invention comprises the step of: let at least a column of at least r=x radiation elements irradiate at least partially simultaneously, in particular simultaneously, said corresponding x samples, wherein said N=x.

Preferably the method according to the present invention comprises the steps of: performing at least partially simultaneously, in particular simultaneously, the previously described step for each column of radiation elements and corresponding samples.

Preferably the method according to the present invention comprises the steps of: splitting the sample radiation of said N samples into spectral components, each component representing the sample radiation, which corresponds to one of said groups of samples; and transmitting each of said components of sample radiation towards a detection unit.

Preferably the method according to the present invention comprises the step of: demodulating said sum signal and evaluating the sample radiation of, each individual sample of said N samples.

Preferably the method according to the present invention comprises the steps of: providing a total number of, in particular n−1, positioning steps of the radiation device relative to the sample holder member, in order to perform a complete scan of the samples by each type of radiation element.

Further, using the explanations and definitions of the description of the present invention, the following embodiments of the method according to the present invention are provided.

The method according to the present invention wherein said N basic frequencies are chosen from a frequency range of 0 kHz to 1 MHz.

The method according to the present invention wherein said reference frequency is at least an order of magnitude higher than each of said basic frequencies.

The method according to the present invention wherein it comprises a step of filtering the detected sum signal by a highpass filter.

The method according to the present invention wherein it comprises a step of filtering the detected sum signal by a bandpass filter.

The method according to the present invention wherein it comprises a step of digitising said sum signal by sampling with a sampling frequency and quantizing.

The method according to the present invention wherein the sampling frequency is equal or higher than the nyquist frequency.

The method according to the present invention wherein it comprises a step of averaging said sum signal over the time.

The method according to the present invention wherein it comprises a step of filtering said sum signal by a digital high-pass filter prior to demodulation.

The method according to the present invention wherein a demodulation method demodulates the sum signal by multiplying it with the reference frequency, The method according to the present invention wherein a step of sub-sampling is performed after demodulation of the sum signal.

The method according to the present invention wherein said transformation operation is a mathematical operation.

The method according to the present invention wherein said transformation operation is a fourier transformation method.

In analogy to said method, an apparatus for radiometrically investigating N (N is a natural number with N>1) sample radiations of at least two samples, which are caused by the radiation of N emitter elements of at least one radiation element wherein said N emitter elements are emitting radiation during time periods which at least partially overlap, comprises:

a control device, adapted to control said radiation elements and to use N basic frequencies to provide N modulation signals wherein each modulation signal is used to modulate the radiation of a different emitter element, at least one detection device which is adapted to detect the sample radiation of at least two samples as a sum signal during time periods which at least partially overlap, an evaluation device which is adapted to evaluate the sample radiation of an individual sample from said sum signal, wherein the evaluation device is adapted to demodulate the sum signal, to perform a transformation operation to transfer the demodulated sum signal from a time dependent signal into a frequency dependent signal and to determine the quantity of at least one individual sample radiation from the amplitude of said frequency dependent signal in dependency on the basic frequency.

According to another embodiment of the present invention, a method for radiometrically investigating N (N is a natural number with N>1) sample radiations of at least one sample, which are caused by the radiation of N emitter elements of at least one radiation element wherein said N emitter elements are emitting radiation during time periods which at least partially overlap, comprises the steps:

determining one code sequence of pseudorandom numbers,
modulating the radiation which is to be emitted by each of said N emitter elements with an individual modulation signal which is formed by using said one code sequence of pseudorandom numbers,
wherein the pseudorandom number code of an individual modulation signal is shifted about at least one bit against the pseudorandom number codes of the other modulation signals,
detecting the N sample radiations as a sum signal wherein each sample radiation is modulated according to the modulated radiation which caused the respective sample radiation,
performing a mathematical operation on said sum signal to decode it,
determining the quantity of at least one individual sample radiation from the decoded sum signal.

Said method according to the present invention offers the particular advantage that the radiation signal which is modulated by the modulation signal and a potential interfering signal, which can be in particular a low frequency interference, have a different time characteristics, which reduces the disturbing of the radiation signal by the potential interfering signal. In particular, the frequency band which is used for the modulation, is positioned at much higher frequencies compared with the frequencies of potential interference signals. Thus, the S/N of the detected quantity of a sample radiation is improved. Moreover, by using different modulation signals, it is possible to address a specific emitter of sample radiation, e.g. a fluorescence marker, or to address a specific sample of the plurality of samples. By said addressing, the sample radiation of a specific emitter of sample radiation or a specific sample becomes discriminable within the sum of N sample radiations which is detected. In contrast to a sequential operation of detection of N sample radiations, the parallel measuring of N different sample radiations offers the possibility to reduce the overall detection time of said N sample radiations which means that the overall measuring time can be reduced.

The code sequence of said pseudorandom numbers is preferably a Gold-code. However, it is possible and preferred that said code sequence is chosen from other sequences which are used in spread spectrum systems, e.g. maximal length sequences, Kasami sequences, Barker codes and the like. The length of the code is preferably at least $2^{N-1}-1$, where N is the number of samples to be monitored during time periods which at least partially overlap.

For the description of code sequences and other technical terms it is referred to the book of Don Torrieri "Principles of spread-spectrum communication systems", Springer, 2005, which is incorporated herein by reference.

It is possible and preferred that another code division multiple access (CDMA) method is used to modulate the radiation of at least two radiation elements during time periods which at least partially overlap and to evaluate the sum of sample radiations which is caused by said at least two radiation elements.

The evaluation device preferably comprises a decoding device, e.g. a correlator device or a multiplicator device, for performing said mathematical operation which is the decoding operation. The decoding operation preferably comprises a correlation operation, e.g. autocorrelation, or a multiplication, to resolve the quantity of the sample radiation from said sum signal.

It is a particular advantage of using said correlation method that the hardware implementation of said correlation method is easier and the calculation time which is required to apply said correlation method can be reduced compared with an FFT operation.

Using the explanations and definitions of the description of the present invention, the following embodiments of the method according to the present invention are provided:

The method according to the present invention wherein the code sequence of pseudorandom numbers is a Gold-code.

The method according to the present invention wherein the mathematical operation comprises a correlation method for correlating the sum signal with an individual modulation signal.

The method according to the present invention wherein said correlation method is autocorrelation-type.

The method according to the present invention wherein said mathematical operation substantially is substitutable by addition and subtraction operations.

In analogy to said method, an apparatus for radiometrically investigating N (N is a natural number with N>1) sample radiations of at least one sample, which are caused by the radiation of N emitter elements of at least one radiation element wherein said N emitter elements are emitting radiation during time periods which at least partially overlap, comprises:

a control device, adapted to control said radiation elements and to modulate the radiation which is to be emitted by each of said N emitter elements with an individual modulation signal which is formed by using said one code sequence of pseudorandom numbers,
wherein the pseudorandom number code of an individual modulation signal is shifted about at least one bit against the pseudorandom number codes of the other modulation signals,
at least one detection device which is adapted to detect the sample radiation of at least one samples as a sum signal during time periods which at least partially overlap,
an evaluation device which is adapted to evaluate the sample radiation of an individual sample from said sum signal,
wherein the evaluation device is adapted to decode said sum signal by a mathematical operation and
wherein the evaluation device is adapted to determine the quantity of at least According to a further embodiment, a method for radiometrically investigating N (N is a natural number with N>1) sample radiations of at least one sample, which are caused by the radiation of N emitter elements of at least one radiation element wherein said N emitter elements are emitting radiation during time periods which at least partially overlap, comprises the steps:

determining a set of N Hadamard-code-sequences wherein each of said Hadamard-code-sequences is used to form an individual modulation signal, modulating the radiation which is to be emitted by each of said N emitter elements with a different individual modulation signal, detecting the N sample radiations as a sum signal wherein each sample radiation is modulated according to the modulated radiation which caused the respective sample radiation, performing a mathematical operation on said sum signal to decode it, determining the quantity of at least one individual sample radiation from the decoded sum signal.

Said method according to the present invention offers the particular advantage that the radiation signal which is modulated by the modulation signal and a potential interfering signal, which can be in particular a low frequency interference, have a different time characteristics, which reduces the disturbing of the radiation signal by the potential interfering signal. In particular, the frequency band which is used for the modulation, is positioned at much higher frequencies compared with the frequencies of potential interference signals. Thus, the S/N of the detected quantity of a sample radiation is improved. Moreover, by using different modulation signals, it is possible to address a specific emitter of sample radiation, e.g. a fluorescence marker, or to address a specific sample of the plurality of samples. By said addressing, the sample radiation of a specific emitter of sample radiation or a specific sample becomes discriminable within the sum of N sample radiations which is detected. In contrast to a sequential operation of detection of N sample radiations, the parallel measuring of N different sample radiations offers the possibility to reduce the overall detection time of said N sample radiations which means that the overall measuring time can be reduced.

Said correlation method is preferably autocorrelation-type and preferably backtransforms the sum of N sample radiations using the Hadamard-Matrix which comprises said N Hadamard-code-sequences. In particular, a Walsh-Hadamard-Transform can be used. It is a particular advantage of using said correlation method that the hardware implementation of said correlation method is easier and the calculation steps which are required to perform said correlation method can be performed faster compared with a classic FFT analysis. In a preferred embodiment, signal analysis is performed by a matrix multiplication of the signal vector with the inverse Hadamard Matrix $H^{-1}$. $H^{-1}$ can be calculated once from the Hadamard sequence matrix H and may be stored fixed in the operational software or data memory. This allows for a universal applicability of the method and an easy implementation.

Using the explanations and definitions of the above description of the method according to the present invention, the following embodiments of the method according to the present invention are provided:

The method according to the present invention wherein said Hadamard-code-sequences are orthogonal.

The method according to the present invention wherein the mathematical operation comprises a correlation method for correlating the sum signal with an individual modulation signal.

The method according to the present invention wherein said correlation method is autocorrelation-type.

The method according to the present invention wherein said mathematical operation substantially is substitutable by addition and subtraction operations.

The method according to the present invention wherein said correlation method backtransforms the sum signal by using the inverse Hadamard-Matrix which is related to said N Hadamard-code-sequences.

The method according to the present invention wherein said correlation method uses a Walsh-Hadamard-Transform.

In analogy to said method, an apparatus for radiometrically investigating N (N is a natural number with N>1) sample radiations of at least one sample, which are caused by the radiation of N emitter elements of at least one radiation element wherein said N emitter elements are emitting radiation during time periods which at least partially overlap, comprises:

a control device, adapted to control said radiation elements and to modulate the radiation of said N emitter elements by a set of N Hadamard-code-sequences wherein each of said Hadamard-code-sequences is used to form an individual modulation signal, at least one detection device which is adapted to detect the sample radiation of at least one samples as a sum signal during time periods which at least partially overlap, an evaluation device which is adapted to evaluate the sample radiation of an individual sample from said sum signal, wherein the evaluation device is adapted to decode said sum signal by a mathematical operation and wherein the evaluation device is adapted to determine the quantity of at least one individual sample radiation from the decoded sum signal.

The methods according to the present invention offer the advantage that the measurement is less sensitive for extraneous light which might interfere with the detected sample radiations. Generally, the interference liability is reduced by the methods according to the present invention. In particular, the inherent noise of the detection unit can be suppressed at least in part by the methods according to the present invention.

Further advantages, features and applications of the present invention can be derived from the following embodiments of the apparatus and the methods according to the present invention with reference to the drawings. In the following, equal reference signs substantially describe equal devices.

Figure 1:
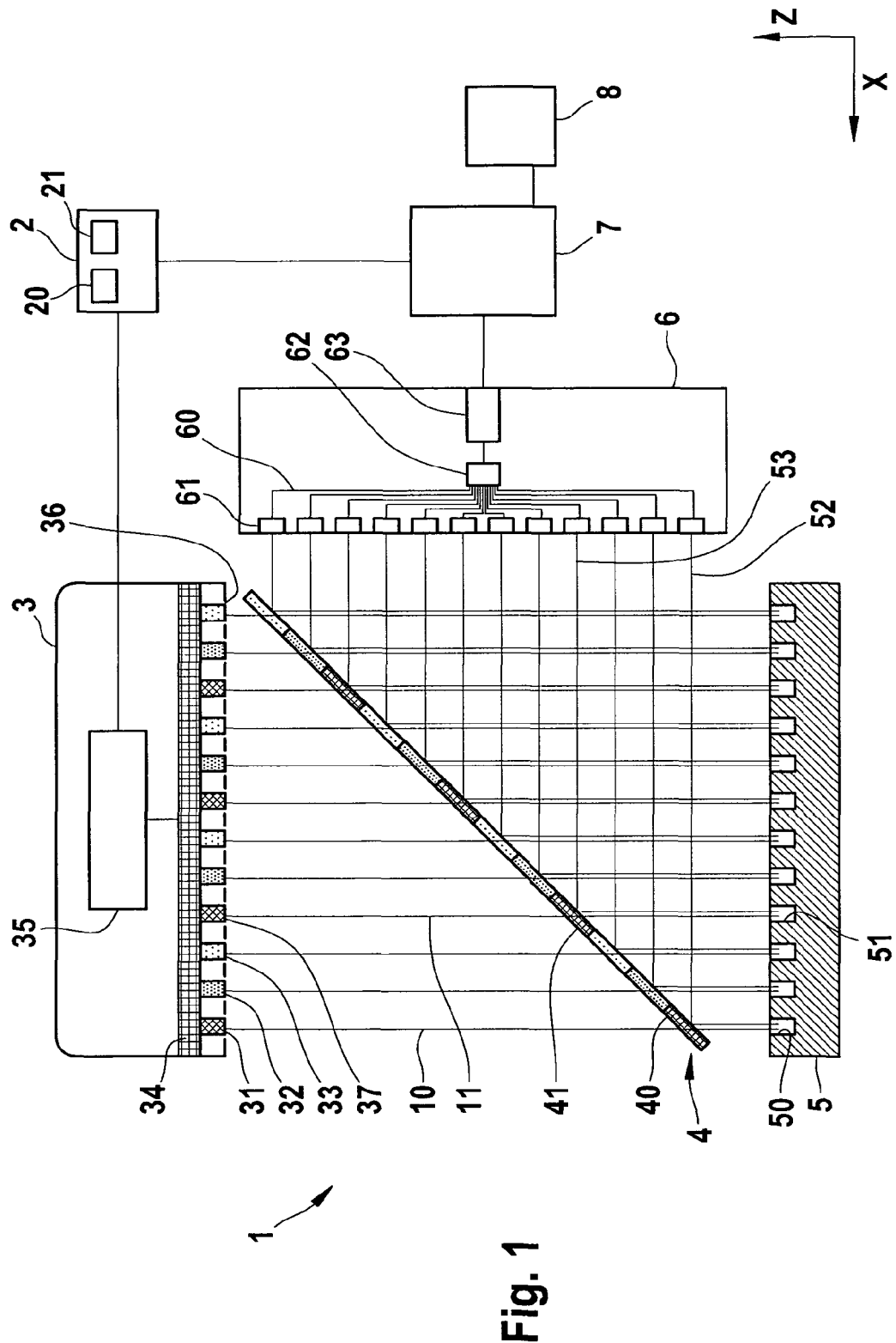
FIG. 1 shows a schematic view of an embodiment of the apparatus according to the present invention.

FIG. 1 shows a schematic view of an embodiment of the apparatus 1 according to the present invention. The apparatus of the embodiment is an apparatus for photometrically measuring the quantity of fluorescence of fluorescent samples in realtime PCR. The apparatus 1 comprises a control device 2 which is connected to the radiation device 3 and the evaluation device 7, the radiation device 3 being in optical connection with the sample holder member 5 via the auxiliary device 4, the sample holder member 5 being in optical connection with the detection device 6 via the auxiliary device 4, an evaluation device 7 connected to the detection device 6 and a computer device 8 for further evaluation and visualisation of the data and preferably, for the configuration of the apparatus, connected to the evaluation device 7.

As further shown in FIG. 1, the control device 2 comprises a power supply unit 21 which supplies the required supply voltages to the control device. The control device 2 is connected to a circuitry substrate 34 to activate the LEDs 31, 32 and 33 of the radiation device 3 according to a specific operational scheme. The operational scheme comprises a step of activating at least two LEDs during time periods which at least partially overlap. Said LEDs can be the same type of LEDs because the apparatus preferably is capable to use the same type of LEDs in a parallel operation mode by detecting a sum of sample radiations in a sum signal and to derive the strength of an individual sample radiation from said sum signal.

As further shown in FIG. 1, the radiation device 2 comprises the circuitry substrate 34 to control the individual LEDs 31, 32 and 33. The control device preferably comprises further control means 35 which preferably can be used to at least partially control supplementary elements of the control device 2. Supplementary elements might be for example temperature sensors or active or passive coolers which serve in particular to keep the temperature of the control device 2 and in particular the temperature of the LEDs 31, 32 and 33 on a defined value.

As further shown in FIG. 1, the radiation device 2 comprises 96 LEDs which can be white or blue LEDs. At least, it is possible that at least one LED is a white or a blue LED. At hand, three different types of LEDs 31, 32 and 33 are shown, e.g. green, red and yellow LED. Each type of LED preferably has a characteristic narrowband light emission spectrum which preferably is adapted to efficiently excite a preferred type of fluorescence marker. The LEDs are arranged substantially two-dimensional in an LED array with 12 rows and 8 columns which preferably corresponds to the geometry of a commercial 96 well plate or microtiter plate. However, other arrangements of LEDs might be applicable as well, for example star-shaped, circular or otherwise patterned arrangements. FIG. 1 shows substantially the schematic view of a cross section through one column of the LED array. Each row preferably provides the same type of LED. The light of each LED leaves the radiation device 2 through an aperture 36 which might be equipped with a lens to direct the light, or a filter or other optical means to influence a property of said light.

Respective to FIG. 1, in an exemplary but simplified operational mode, the control device 2 addresses the light of two LEDs 31, 37 by modulation signals and evaluates the resulting sum signal in synchronisation with the LED-activity: the light is directed during time periods which at least partially overlap, along the first optical path 10 of the first LED and a further first optical path 11 of a second LED, transmitting the auxiliary device 4 through the mirror elements (segments) 40 and 41, towards the sample holder member 5, into a receptacle 50 and a receptacle 51, which each contain a sample with the same type of fluorescence marker. The fluorescence marker of each sample is excited to emit a sample radiation during said time periods which at least partially overlap. The sample radiations, which have spectra which differ from the respective excitation radiation spectra, are emitted via the second optical paths 52, 53 towards the dichroic mirror elements (segments) 40 and 41, where they are reflected and directed towards the detection device 6. The detection device 6 detects the sample radiation of both receptacles 50, 51 during said time periods, which at least partially overlap, and superimposes the detected radiations into an electrical sum signal. Said sum signal is evaluated by the evaluation device. The evaluation device 7 uses a multiplexing method, in particular a method according to the present invention, to resolve the quantity of each sample radiation from said sum signal by transforming the sum signal in dependency on the modulation signals by a transformation operation.

Respective to FIG. 1, repetitions of this measurement allow to monitor the amount of fluorescence marker which is formed in the receptacles 50, 51 over the time and to collect, modify and display the data with a computer device 8. In quantitative realtime PCR, the concentration of fluorescent markers in the sample is changing in dependence on the progress of the PCR-reaction. The apparatus and the method according to the present invention provides a short overall measuring time. Therefore, more data of the concentrations which are monitored over the time (the kinetics) can be collected within a predetermined period. This means, the resolution of the kinetics is improved which allows for a more precise control of the PCR process. In contrast to the simplified description in this paragraph, preferably 8 or 16 LEDs are exciting 8 or 16 samples whose fluorescence is detected, during time periods which at least partially overlap, and the sum signal of said 8 or 16 sample fluorescences is evaluated to resolve the individual quantity of fluorescence from each sample. However, another number than 8 or 16 of simultaneously active LEDs and detected sample radiations is possible within the scope of the present invention.

As further shown in FIG. 1, the auxiliary device 4 at hand is a mirror section, in particular a mirror section consisting of 12 mirror segments, wherein three mirror segments are different in correspondence to the respective LEDs 31, 32, 33 and the respective sample radiations. Each mirror segment consists of 8 equal mirror elements wherein the 8 mirror elements are integrally formed as one mirror segment which corresponds to one row of LEDs. The mirror elements are dichroic mirrors which are appropriate to be used as a beamsplitter. A beamsplitter transmits the appropriate (excitation) radiation light and reflects the fluorescence (emission) light (sample radiation) of the sample, in dependence on the respective spectral ranges of excitation and emission. The design of the auxiliary device is adapted to allow to direct radiation via a plurality of first and second optical paths, which allows to detect and measure said sum signal.

As further shown in FIG. 1, the sample holder member 5 is a thermoblock which is adapted to hold 96 samples and to adjust the temperature of the samples. The adjustment of the temperature can be performed by means of further controllers, the control device 2, the evaluation device 7, the computer device 8 or other devices. The 96 samples might be placed in 96-standard microtiter plates (MTP) which are used in PCR applications. The sample holder member includes a lid which is not drawn here, whose temperature is preferably adjustable and mountable, preferably on top of the receptacles of the sample holder member. Such a lid prevents the undesired exchange of matter between the inner and the outer side of the receptacles, avoiding evaporation and contamination. The lid provides 96 optical windows, e.g. transparent plastic windows, which are arranged above the receptacles.

As further shown in FIG. 1, the detection device 6 has an optical device 60, which is an array 60 of optic fibers. The optical fiber array 60 catches the sample radiations from the samples reflected by the mirror section 4 by means of the mutually spaced light input areas 61 and harnessing optic fibers so as to transmit the light through parallel harness ends at 62. Additional optical means at 62 might guide the superimposed sample radiations towards the detector 63, e.g. a photomultiplier, where they are converted to an electrical sum signal. The sum signal is then further processed by the detection device by means which are not shown here: amplified, preferably by a transimpedance amplifier device, filtered, preferably by a band pass, and converted by sampling with a sampling device and digitising by an A/D-converter. The sum signal is input in the evaluation device, where the quantity of each specific sample radiation, e.g. the amplitude of each sample radiation, is calculated from said sum signal by a mathematical operation.

Figure 2:
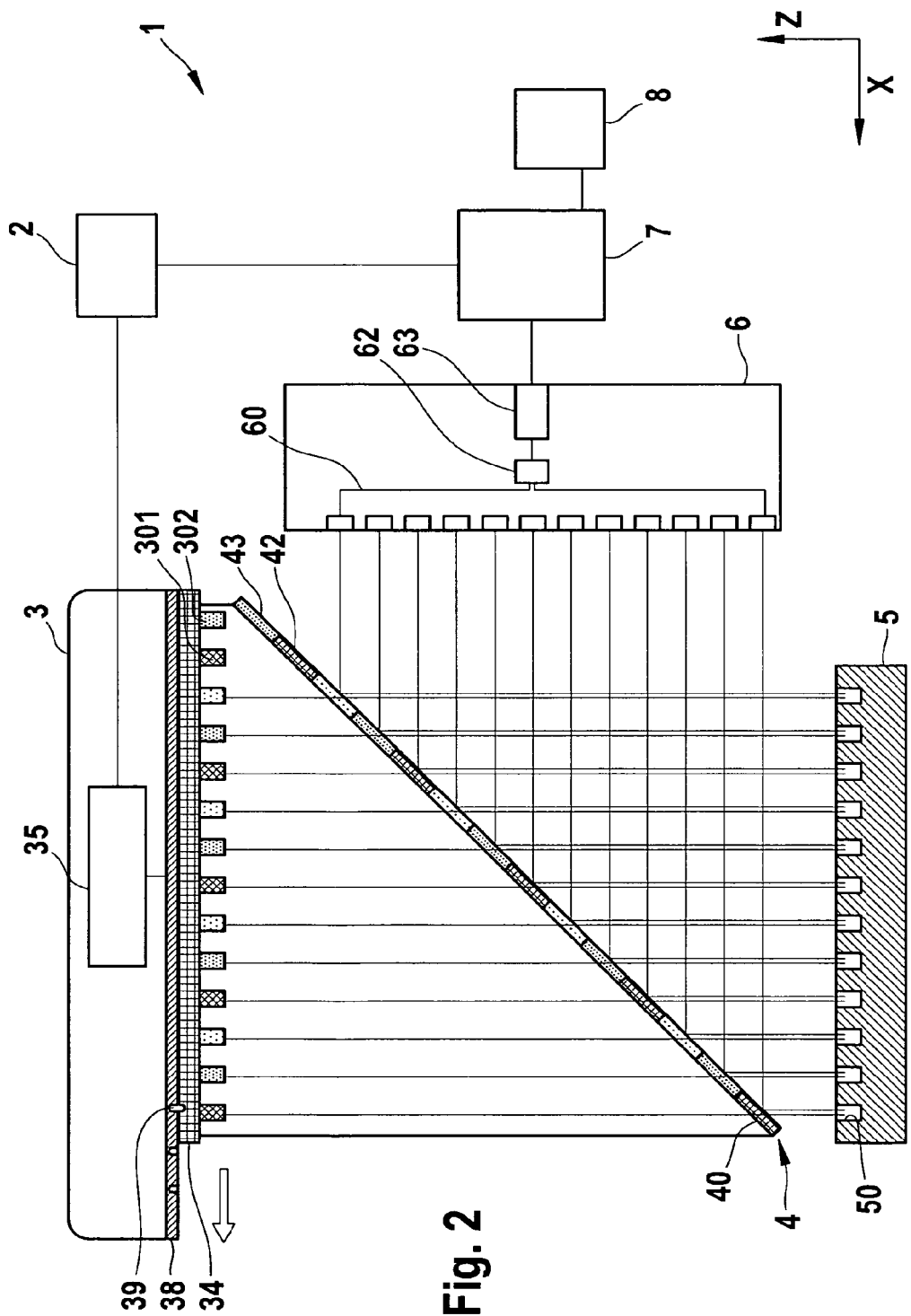
FIG. 2 shows a schematic view of another embodiment of the apparatus according to the present invention.

FIG. 2 shows a schematic view of another embodiment 1 of the apparatus according to the present invention. In this embodiment, the circuitry substrate 34 which carries the LEDs and the mirror section 4, which is mounted to the substrate 34, are movable along the X-direction by motion means 38, e.g. comprising a linear motor. Preferably, locking means 39 are provided at predetermined positions along the motion means 38 and at the substrate 34, to enhance the precision of the positioning. Further, the setup of the apparatus according to the embodiment of FIG. 2 is similar to the setup in FIG. 1. However, the LED matrix in FIG. 2 has two additional rows 301, 302 and the mirror section 4 has two additional segments 42, 43, each having 8 mirror elements corresponding to the respective LEDs in the rows 301, 302. As an advantage of this design, from the start position of the substrate 34, which is shown, only two steps of motion along the X-direction are required to irradiate each sample with each type of LED-light. Thus, the positioning error decreases and the measurements become more precise. In addition, the motion means 38 can be constructed smaller and are less costly.

Figure 3:
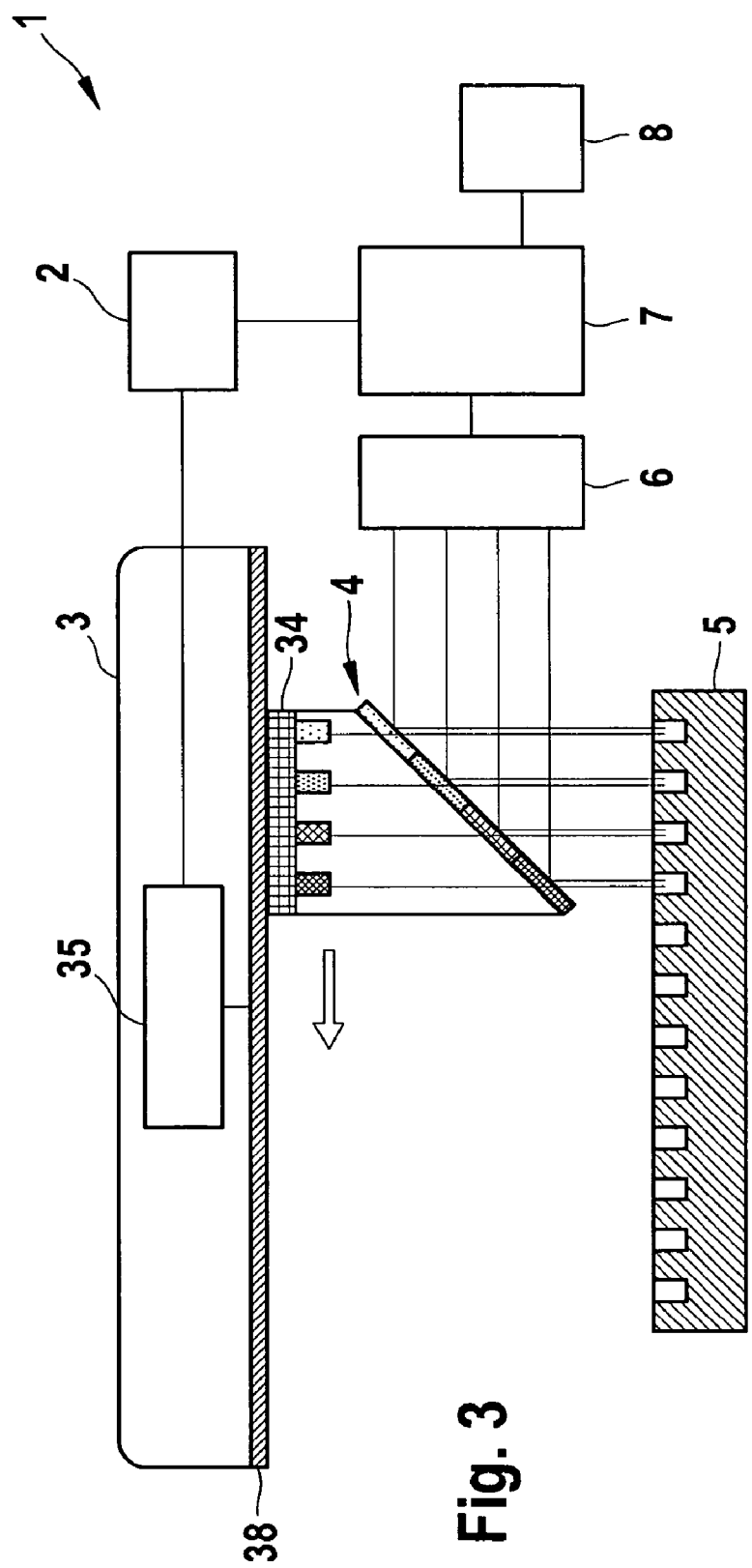
FIG. 3 shows a schematic view of another embodiment of the apparatus according to the present invention.

FIG. 3 shows a schematic view of another embodiment 1 of the apparatus according to the present invention. In this embodiment, similar to FIG. 2, the circuitry substrate 34 which carries the LEDs, is movable along the X-direction by motion means 38, e.g. comprising a linear motor. The embodiment here uses four different types of LEDs which might be adapted to four different types of fluorescence markers in the samples. As an advantage of this design, much less LEDs are required. In consequence, maintenance and performance issues of the LEDs are easier to handle. LEDs might have—to a certain amount—individual performance characteristics, e.g. relating to the radiation flux or the spectrum. Since a smaller number of LEDs is used here, the fluctuations according to different radiation fluxes are reduced, in consequence the corresponding fluctuations in the sample radiations are reduced, and the reliability and comparability of the data improves. As an advantage of the row-like arrangement of the LEDs, from the start position of the substrate 34, only 14 steps of motion along the X-direction are required to irradiate each of 96 samples with each type of LED-light.

Figure 4:
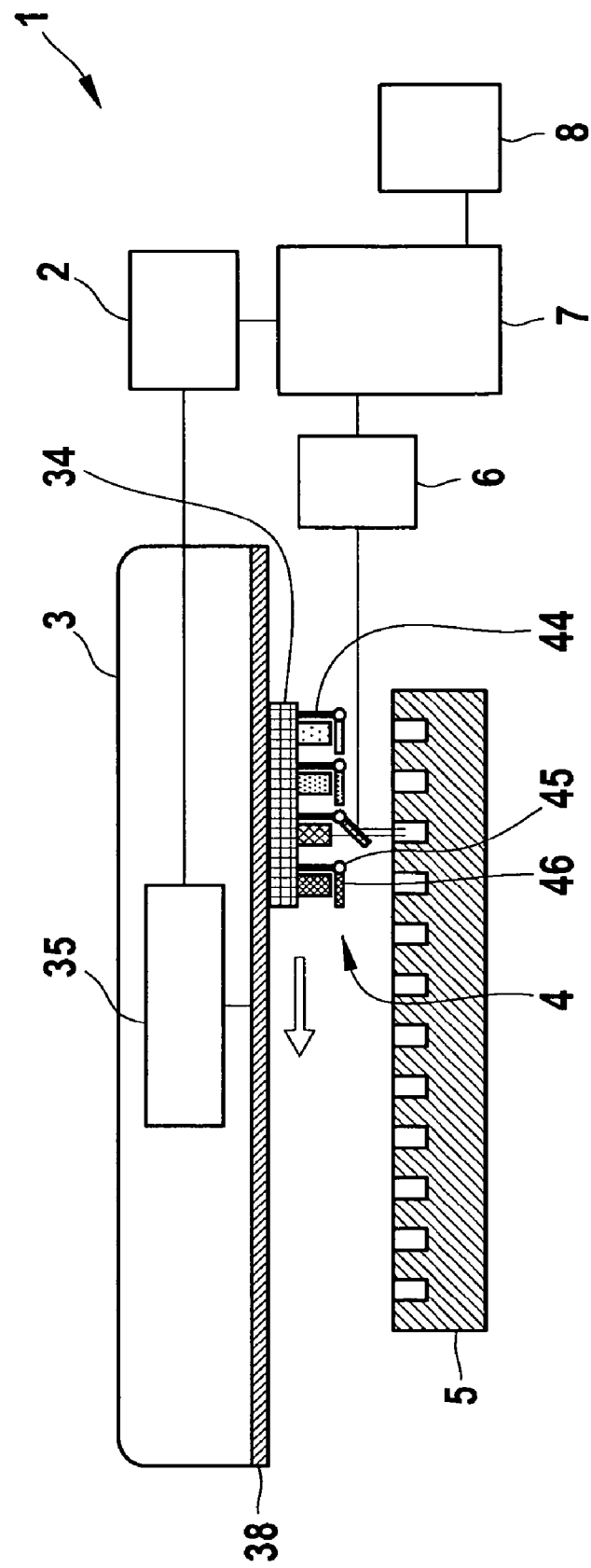
FIG. 4 shows a schematic view of another embodiment of the apparatus according to the present invention.

FIG. 4 shows a schematic view of another embodiment 1 of the apparatus according to the present invention. Different to the embodiment of the apparatus 1 in FIG. 3, the auxiliary device 4 comprises mirror segments 46, which are blade-like elements, pivoted via a motorized hinge 45, which can be controlled via the connection 44 by the supplementary controller 35. The motor of the hinge can be a piezo element, an actuator, linear motor, an electromagnetic switch and the like. The mirror segments 46 have 8 mirror elements each, which correspond to a respective LED. Due to the—compared to FIG. 1-3—shortened distance between LED and sample, the radiation intensity which arrives at the samples is higher, the amount of stray light can be reduced and the radiation as well as the sample radiation can be directed more efficiently. As further advantages, the S/N of the sum signal can be enhanced and the whole setup is more compact.

Figure 5:
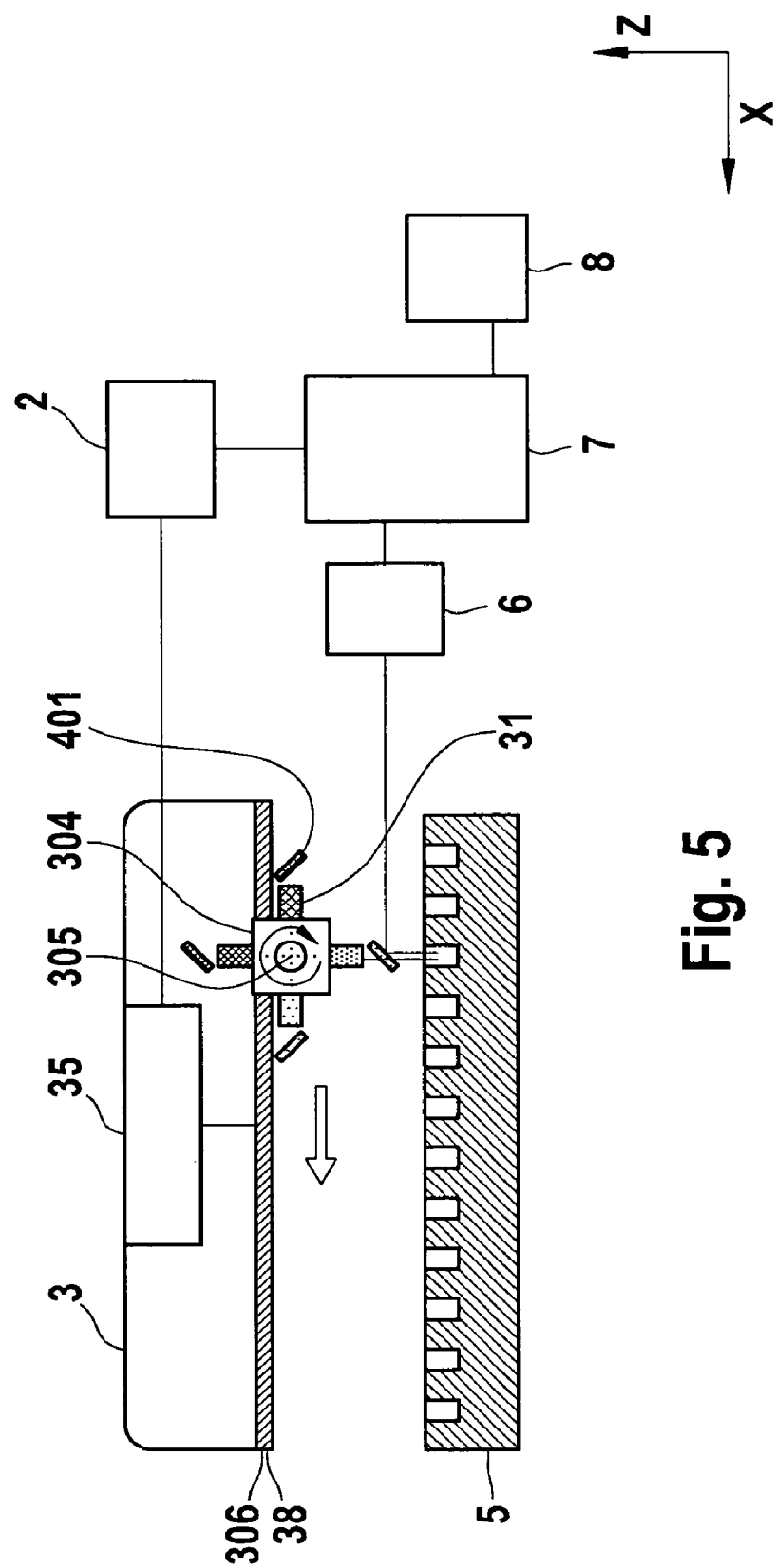
FIG. 5 shows a schematic view of another embodiment of the apparatus according to the present invention.
Figure 6:
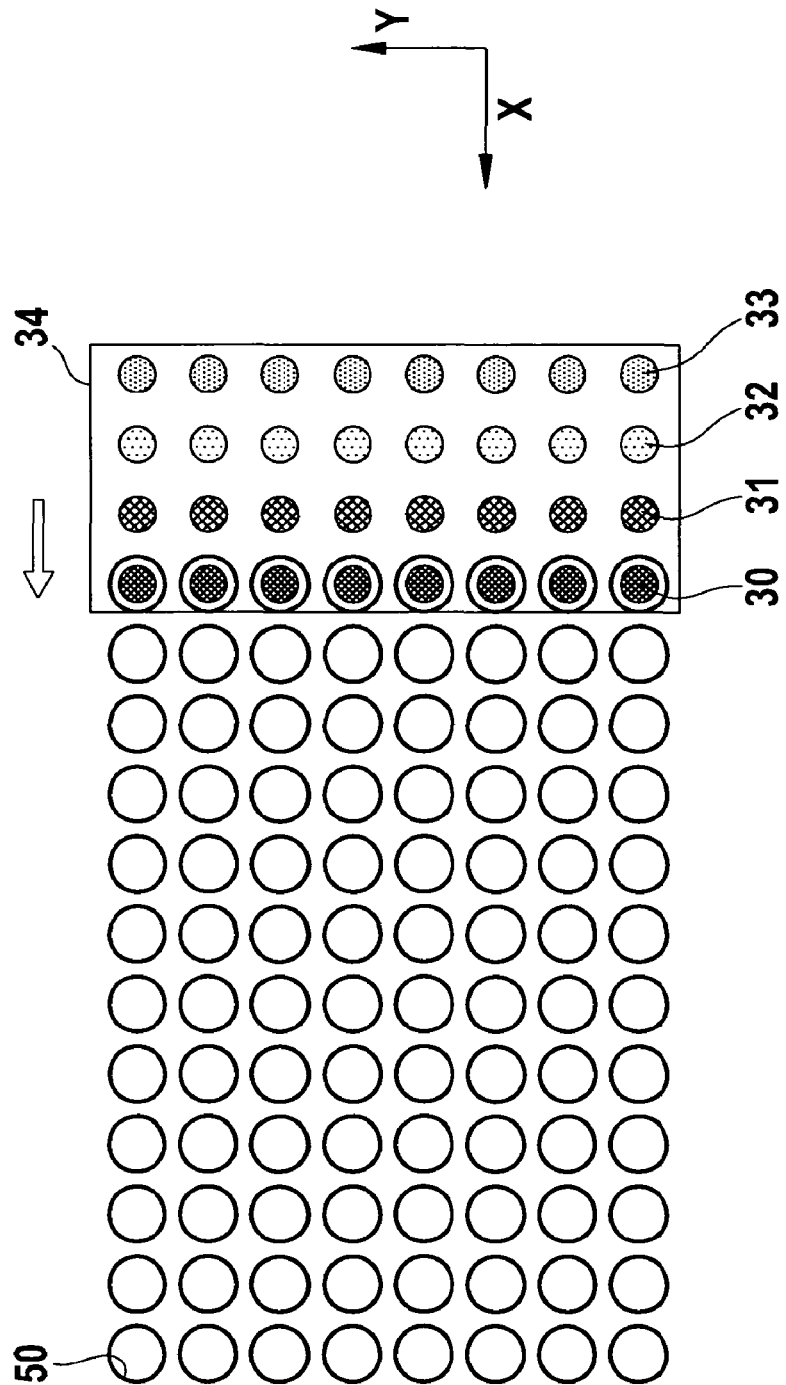
FIGS. 6 to 11 show schematic top views of a different embodiment each of the arrangement of radiation elements of the radiation device of the apparatus according to the present invention respective to the sample position array of the sample holder member.

FIG. 5 shows a schematic view of another embodiment 1 of the apparatus according to the present invention. It differs from the embodiments in FIGS. 3 and 4 by providing a different kind of arrangement of the rows of LEDs 31 and the mirror segments. The 4 rows of 8 LEDs are mounted on a substrate 304 which is mounted rotatably to the support member 306 around an axis of rotation 305, wherein in this embodiment the support member 306 preferably supports said motion means 38 which are not shown here, wherein the axis of rotation 305 is arranged to be aligned in parallel to the support member 306 as well as to the sample holder member 5 and is aligned perpendicular to the X-direction. A motor device which rotates the substrate 304 can be an electromotor which is controlled via the supplementary control device 35. The mirror segments 401 are attached firmly to the substrate 304 and have a fixed position relative to the LEDs. Thus, no positioning step of the mirror elements relative to the LEDs has to be performed. The positioning of the rotatable substrate can be improved by locking means, e.g. detents. This configuration takes profit from a short distance of the LEDs respective to the samples which improves the radiation flux. In a particular embodiment, which is not shown here, the position of the detector device 6 is mounted in a defined distance to the substrate 304, i.e. fixed respective to the axis 305, such that the first and second optical path lengths are even shorter and thus, the radiant flux of the sum signal is even higher.

FIGS. 6 to 11 show schematic top views of a different embodiment of the arrangement of radiation elements, e.g. LEDs, of the radiation device 3 of the apparatus according to the present invention respective to the sample position array of the sample holder member 5. The LED array of FIG. 6 refers to the setup of the apparatus in FIGS. 3 and 4, where 4 rows of LEDs, each row having one type of LED, are present. As an advantage of the row-like arrangement of the LEDs, from the start position of the substrate 34, only 14 steps of motion along the X-direction are required to irradiate each sample with each type of LED-light.

Figure 7:
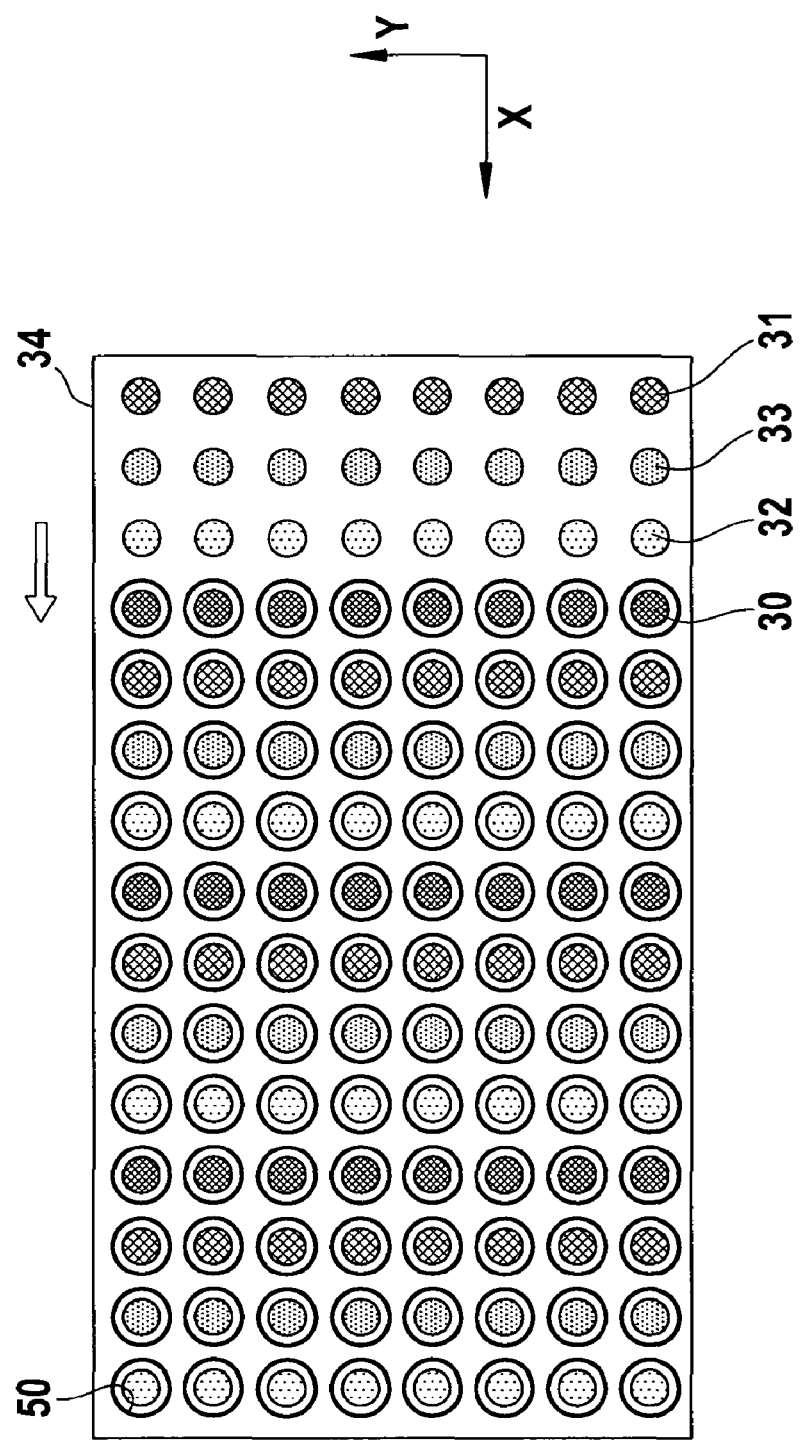

The LED array of FIG. 7 follows the principle of the setup of the apparatus in FIG. 2. In total, 15 rows of the same LEDs with four different types of LEDs are shown. As an advantage of the row-like arrangement of the LEDs, from the start position of the substrate 34, only 3 steps of motion along the X-direction are required to irradiate each sample with each type of LED-light.

Figure 8:
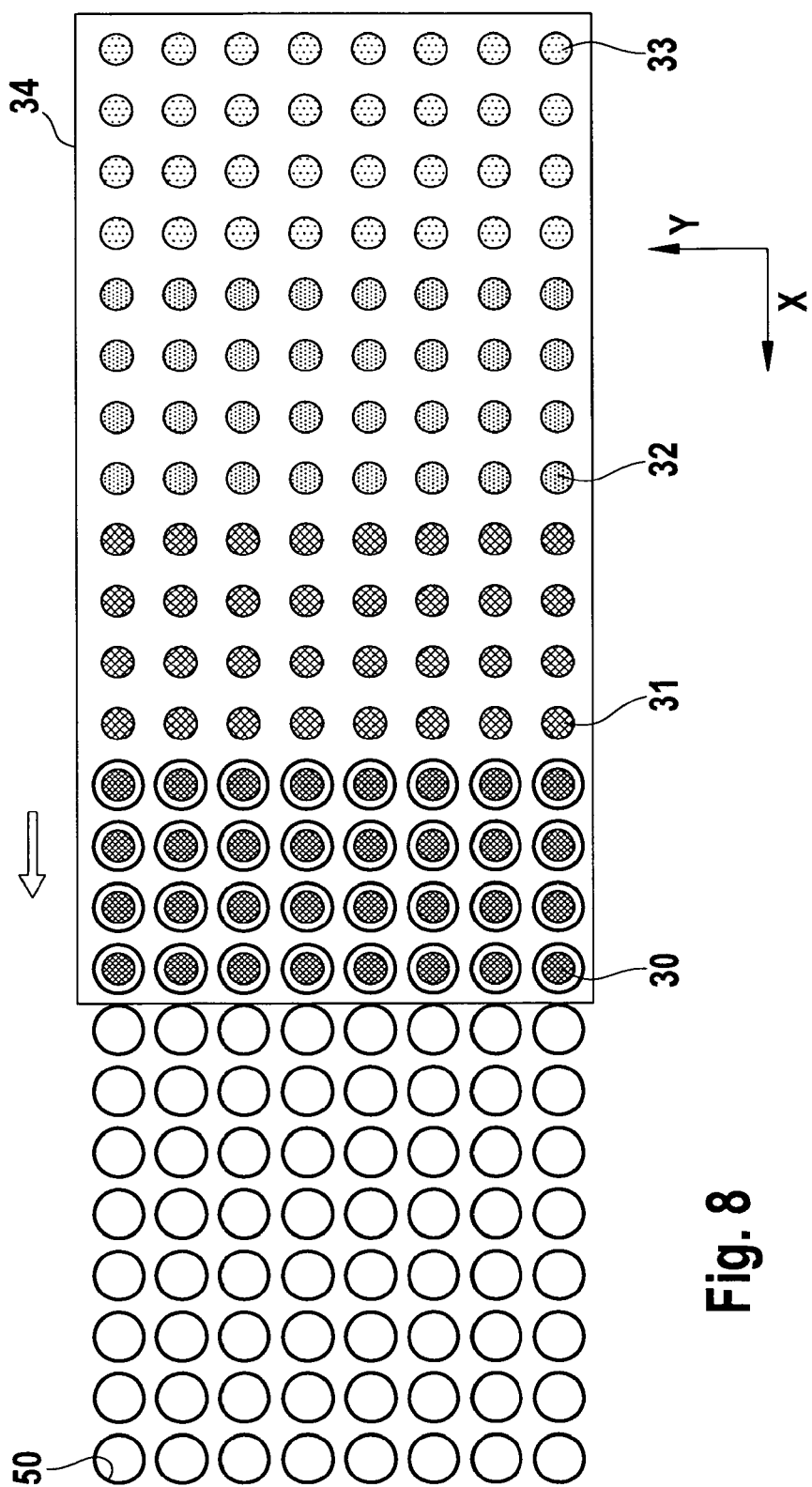

The LED array of FIG. 8 provides LEDs which are arranged in blocks, as an alternative to the row-like arrangement shown in FIGS. 1 to 7. As an advantage of the block-like arrangement of the LEDs, from the start position of the substrate 34, only 3 steps of motion along the X-direction are required here to irradiate each sample with each type of LED-light.

Figure 9:
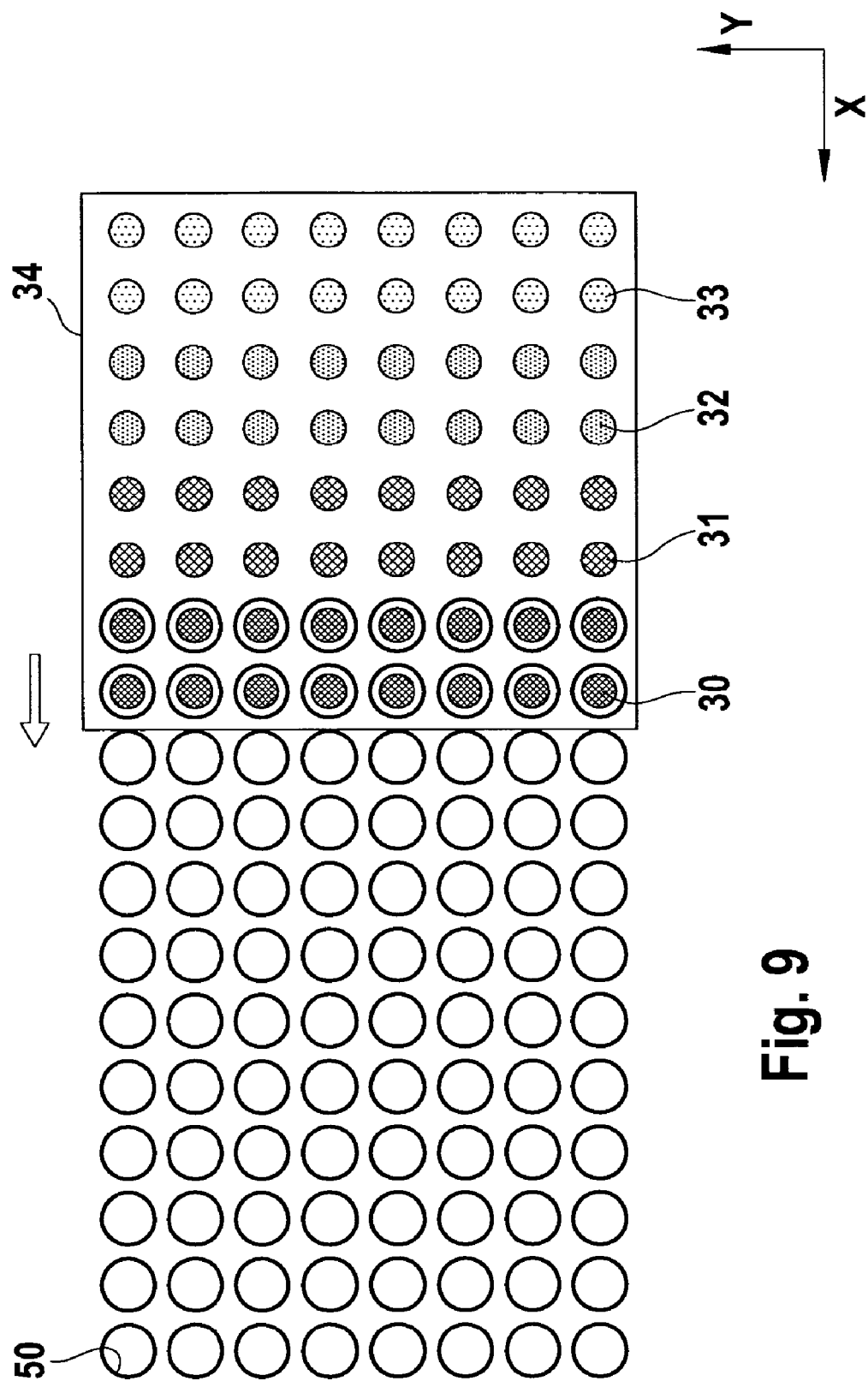

The LED array of FIG. 9 as well provides LEDs which are arranged in blocks. As an advantage of the block-like arrangement of the LEDs, from the start position of the substrate 34, only 8 steps of motion along the X-direction are required here to irradiate each sample with each type of LED-light.

Figure 10:
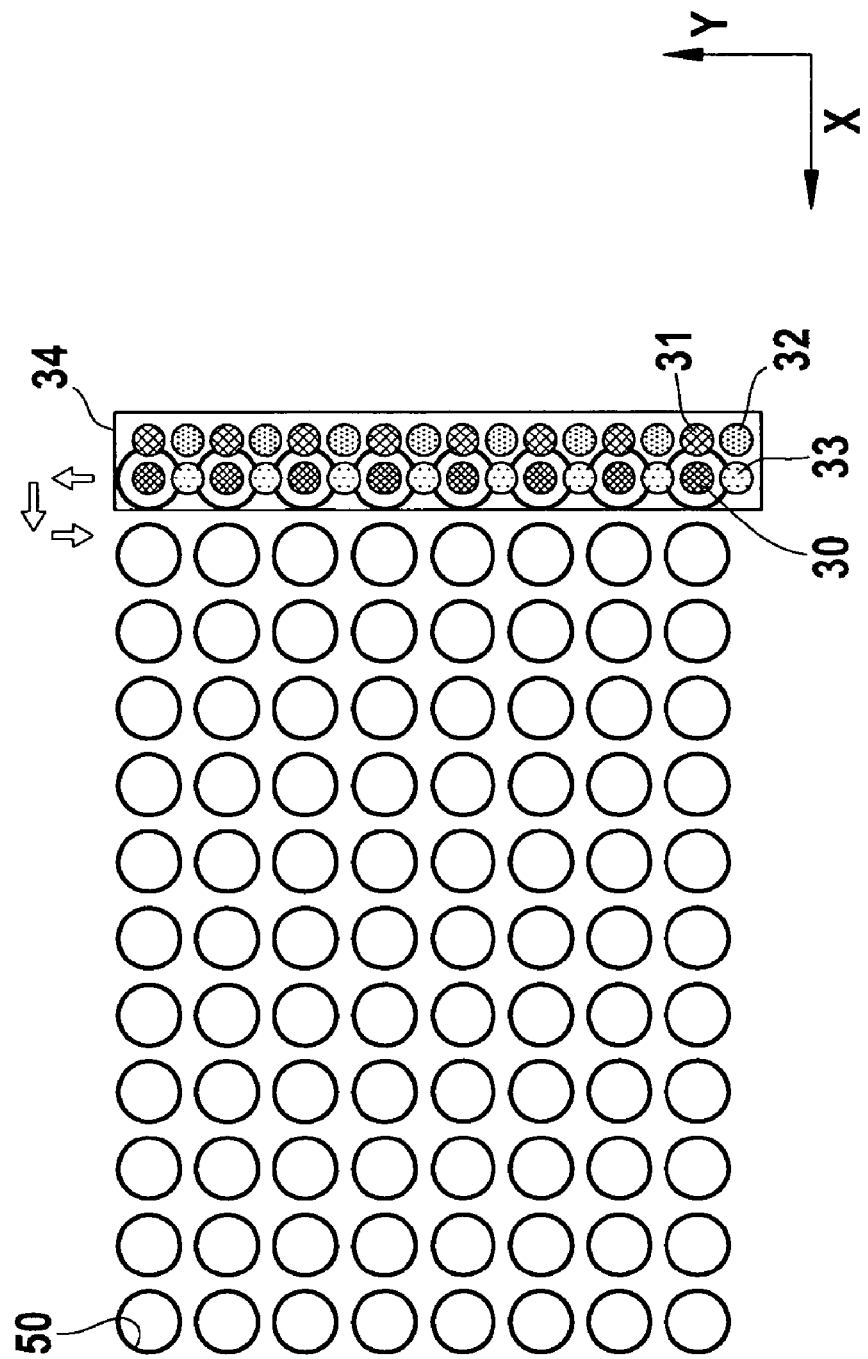

The LED array of FIG. 10 provides a pattern (square) of smaller sized LEDs, e.g. SMD-LEDs, which allow are very compact design of the circuitry substrate 34, as shown. As another advantage of the pattern-like arrangement of the LEDs, from the start position of the substrate 34, as a minimum, only 11 steps with the distance of two samples (center to center) along the X-direction are required. Further, on each of said positions, another three steps of motion along the X- and Y-direction are required here to irradiate each sample with each type of LED-light.

Figure 11:
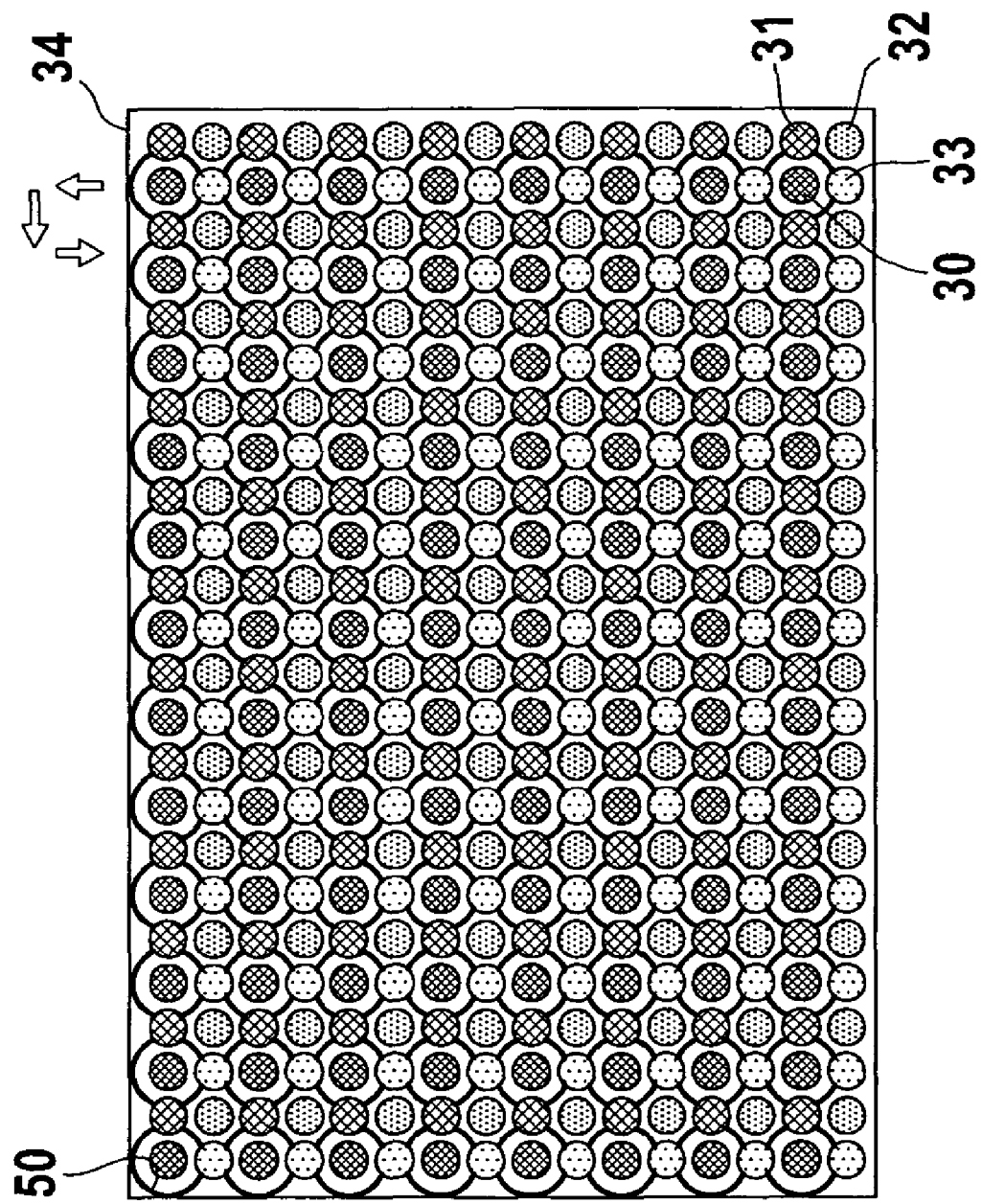

Using an LED arrangement of SMD-LEDs, as shown in FIG. 11, only three steps of motion along the X- and Y-direction are required.

Figure 12:
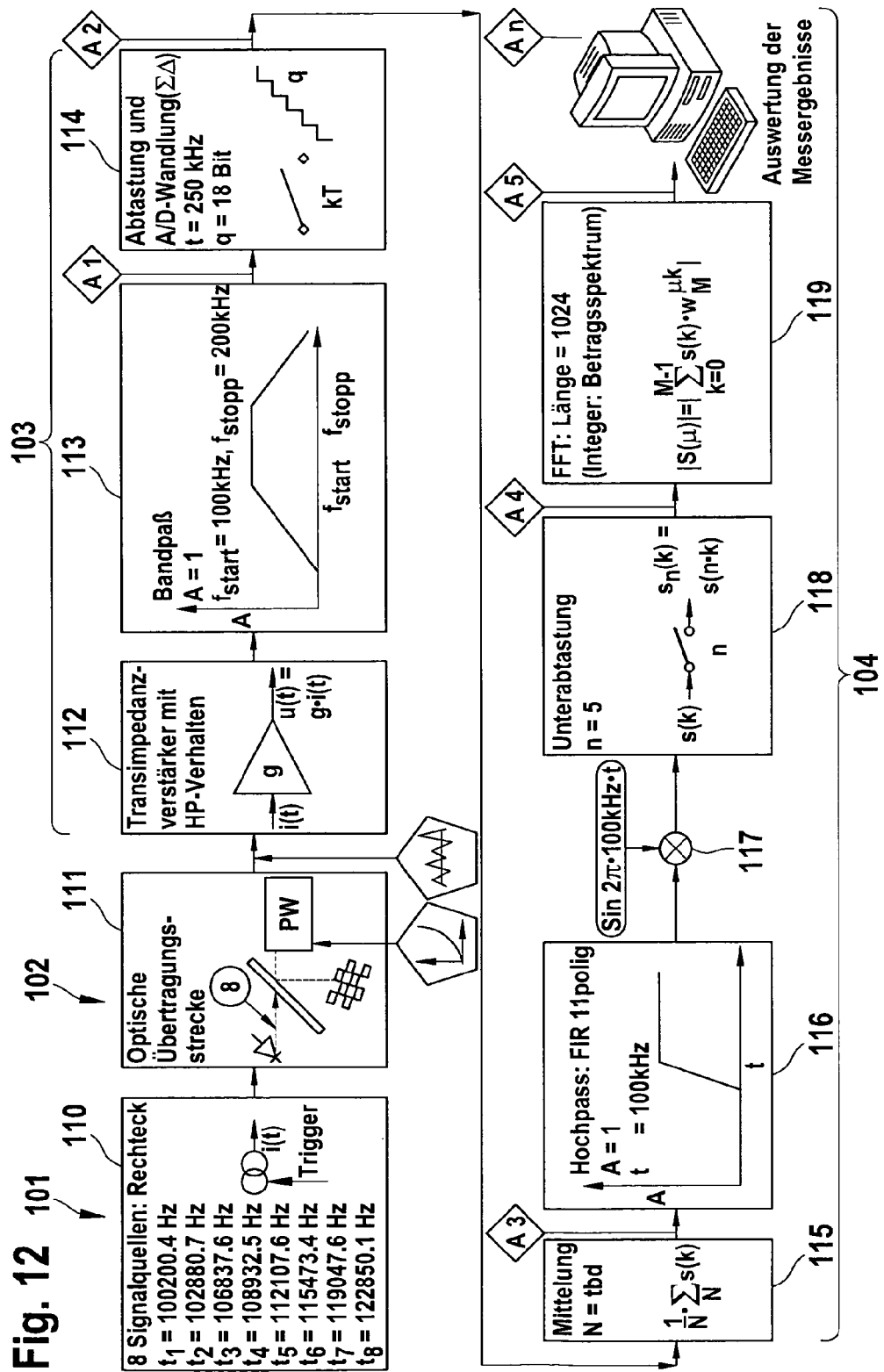
FIG. 12 shows an operation diagram of the embodiment of a method according to the present invention.

FIG. 12 shows an operation diagram of the embodiment of a method according to the present invention. The method is an FDMA method. The method substantially consists of the functional steps of signal generation 101, signal transmission 102, signal reception 103 and signal analysis 104, which are controlled by the control device of the apparatus which uses such a method, in particular the apparatus of the present invention. In the following, a measuring cycle is shown according to the steps (blocks) 110-119.

The FDMA method of FIG. 12 is used to modulate the radiation of 8 LEDs during time periods which at least partially overlap, in particular in parallel, and to evaluate the sum of sample radiations which is caused by the 8 LEDs. At block 110, the light of each LED, taken from said 8 LEDs, is modulated by a modulation signal which has a selected modulation frequency, using square signals and amplitude modulation. The modulation frequencies are generated by adding a fixed reference frequency of 100 kHz by heterodyning to a basic frequency (frequency shifting). Moreover, the basic frequencies are preferably determined such that one basic frequency is not the harmonic of any other basic frequency and that the distance of the basic frequencies is larger than the bandwidth of the spectral line which is determined by a fourier transformation of the modulation signal. Another aspect of adjusting the modulation signals is that they preferably should provide the same quantity (height) of the spectral lines at the end of the process under reference conditions, i.e. after signal analysis. Appropriate modulation frequencies are, for example, 100200.4 Hz, 102880.7 Hz, 106837.6 Hz, 108932.5 Hz, 112107.6 Hz, 115473.4 Hz, 119047.6 Hz and 122850.1 Hz. The method of shifting the address frequencies to the higher values by the reference frequency, which is applied here, helps to avoid the low-frequency noise which in particular is found in the range from 0 kHz to 50 kHz. Moreover, frequency shifting allows a much easier filtering by a relatively narrow-band band-pass (113).

Said 8 LEDs irradiate, substantially in parallel, one sample receptacle each. Thus, 8 sample radiations are generated in parallel, and converted to a time-dependent electric sum signal (in this embodiment a current i(t)) by a photomultiplier, shown in block 111 of FIG. 12. Said current is amplified, and preferably converted to a voltage by the transimpedance amplifier, shown in block 112. Said transimpedance amplifier has the characteristic of a high-pass, such that low-frequency fractions (=noise, interferences) of the signal are attenuated. The band-pass, shown in block 113, has a transmission range according to the modulations frequencies, in this embodiment in the range 100 kHz to 200 kHz, and is a prerequisite for ND-conversion (antialiasing). The sum signal is digitized by sampling the analogue sum signal with a sampling frequency equal or higher than the nyquist frequency, here 250 kHz, by a fast analogue/digital transducer, shown in block 114 of FIG. 12.

The digital sum signal is repeatedly averaged over the time by an averaging device, shown in block 115 of FIG. 12, which acts as another noise suppression means and further improves the signal quality of the digital sum signal. The digital high-pass, shown in block 116, is particularly required in the case that the detector (photomultiplier) shows square non-linearities which can be suppressed by said digital high-pass filter.

In order to simplify the frequency analysis of the digital sum signal, the digital sum signal is demodulated by multiplying it—in phase synchronization with the signal generation and analysis—with a sinus-function which substantially oscillates with the reference frequency, i.e. 100 kHz in this embodiment, shown in block 117 of FIG. 12. Thus, the frequencies are shifted to the base-band, which allows data reduction by a sub-sampling of the sum signal with the factor 5, shown in block 118.

Shown in block 119 of FIG. 12, a fourier transformation, in particular an FFT on 1024 values, transforms the subsampled, time-dependent, digital sum signal into the frequency domain, thus resulting in a signal spectrum, which is a frequency-dependent function. The height of the spectral line which corresponds to a specific modulation frequency is the quantity of the corresponding sample radiation, which quantifies the strength of the sample radiation, and which might be transferred to the additional computer for further evaluation and display of the results. The method of this embodiment offers in particular the advantage that substantially no floating point operation is required to perform the FFT because it is substantially performed in integer mathematics. Thus, a simple processor unit, e.g. an FPGA, can be used as transformation means to perform the mathematical operation. A single integer operation only needs one clock cycle. A typical FPGA can be operated at 100 MHz. Thus, an integer operation lasts 10 ns only, and therefore the FFT of a measurement cycle can be performed faster, in particular compared to prior art methods which require to use floating point operations. Additionally, data reduction by sub-sampling reduces the computation time even more.

Figure 13:
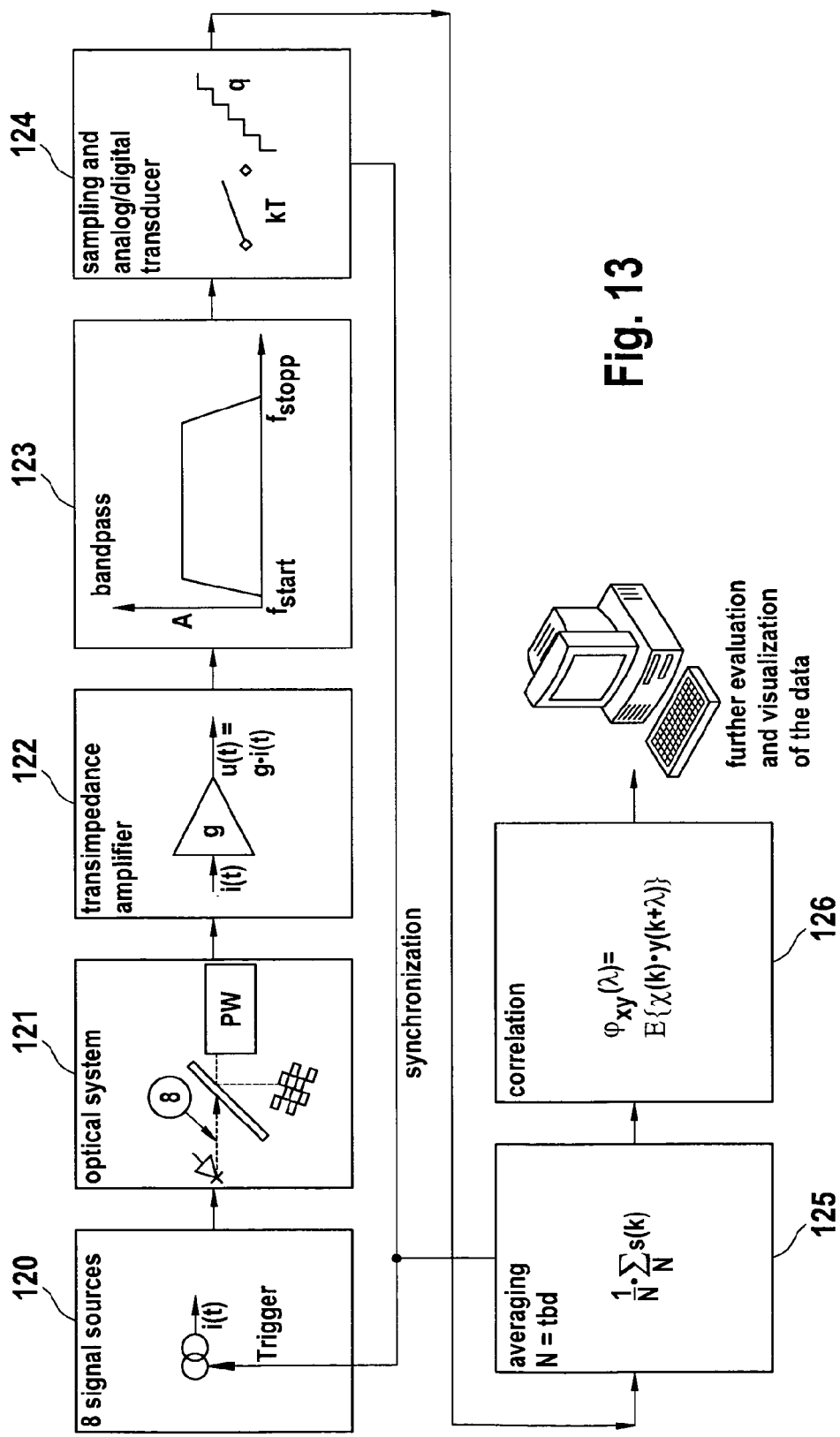
FIG. 13 shows an operation diagram of the embodiment of a method according to the present invention.

FIG. 13 shows an operation diagram of the embodiment of a method according to the present invention. The method is a CDMA method. In block 120, one code sequence of pseudonoise code (pseudorandom number; preferably Gold-code) with a length of 127 (which is calculated by $2^{N-1}-1$, where N is the number of samples to be monitored at least partially simultaneously; N=8 in this embodiment) is used to modulate the light of each of 8 LEDs, which are substantially activated in parallel, by square signals with a reference frequency (carrier frequency) of about 100 kHz. To be able to distinguish the 8 signals, said one code signal is superimposed to the light of the 8 LEDs in a delayed manner which means that the sequence is shifted about at least one clock cycles, preferably 8 clock cycles, from one modulation signal to the next modulation signal. The shifts are in synchronization with the signal analysis by means of a trigger device.

Shown in block 121 of FIG. 13, said 8 LEDs irradiate, substantially in parallel, one sample receptacle each. Thus, 8 sample radiations are generated in parallel, and converted to a time-dependent electric sum signal (current i(t)) by a photomultiplier, shown in block 121 of FIG. 13. Said current is converted and amplified to a voltage by the transimpedance amplifier, shown in block 122. Said transimpedance amplifier has the characteristic of a highpass, such that low-frequency fractions (=noise, interferences) of the signal are attenuated. The ranges of the band-pass are chosen according to the spectral bandwith of the modulation signal, in this embodiment 10 kHz and 900 kHz, shown in block 123. The band-pass is in particular a prerequisite for ND-conversion and is another noise suppression means which improves the sum signal quality (anti aliasing). The sum signal is digitized by sampling the analogue sum signal with at least the nyquist frequency, e.g. 400 kHz in this embodiment, by a fast analogue/digital transducer, shown in block 124 of FIG. 13. The averaging, shown in block 125, uses a lock-in device which monitors the reference frequency in dependence on the start time of the code sequences. The sampling in block 124 and the averaging in block 125 as well as the signal generation in block 120 are synchronized which is triggered by block 125 of the signal analysis. A higher number of averaging cycles are preferably used to improve the S/N of the evaluated signals, regarding the overall measuring time which should be short.

The result of the averaging lock-in filter in block 125 in FIG. 13 is transferred to the correlation means in block 126 which performs a circular correlation operation using the modulation code sequence as a reference. The method of this embodiment offers in particular the advantage that substantially only integer additions (and subtraction operations) have to be performed. Moreover, the signal analysis substantially requires addition and subtraction operations while multiplication operations are substantially not needed. Thus, the signal analysis becomes faster than the FFT of the FDMA-method. Moreover, the code sequences are quite short such that a small FPGA, in particular without an external memory device, can be used for the analysis which reduces costs.

Figure 14:
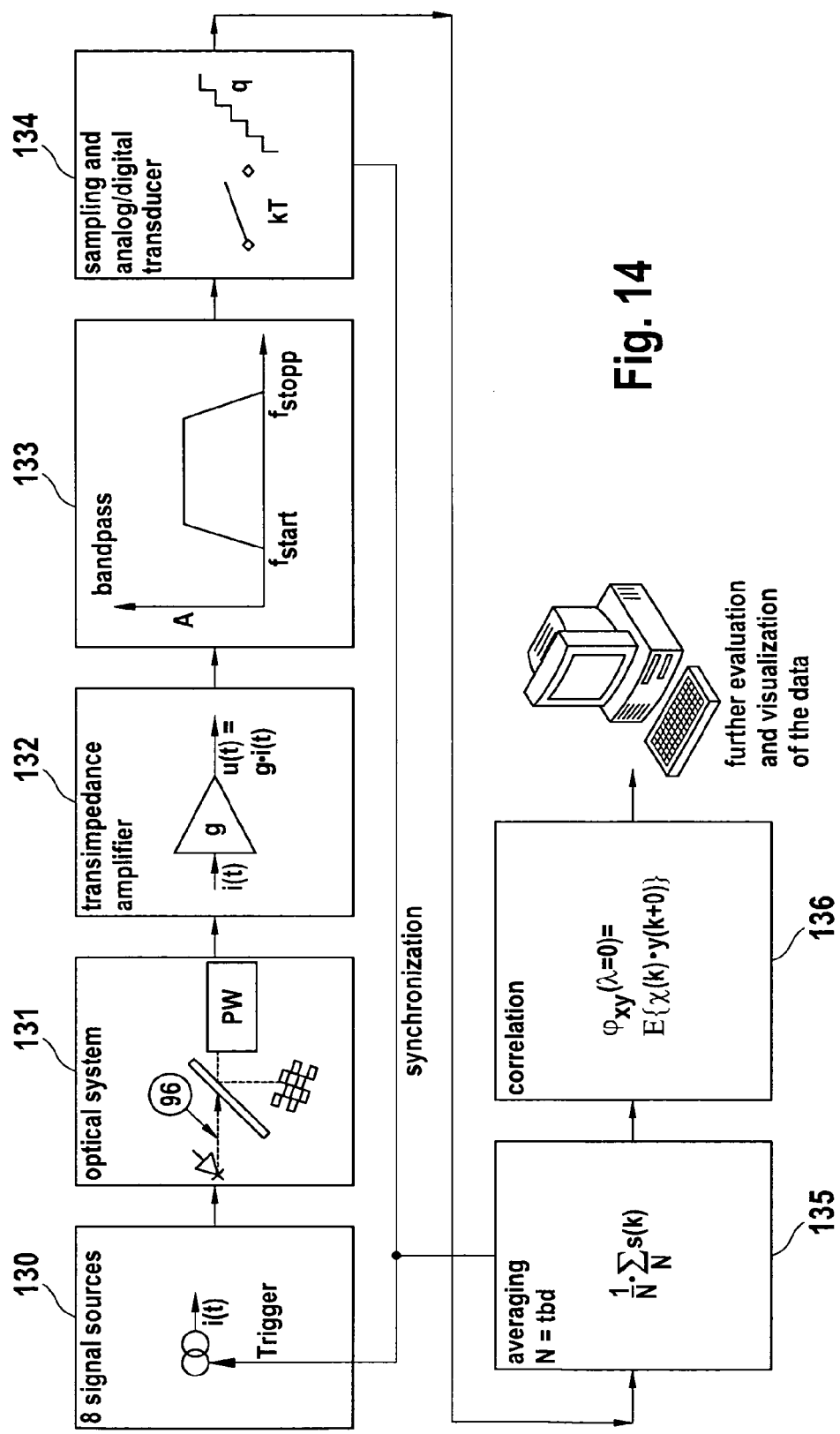
FIG. 14 shows an operation diagram of the embodiment of a method according to the present invention.
Figure 15:
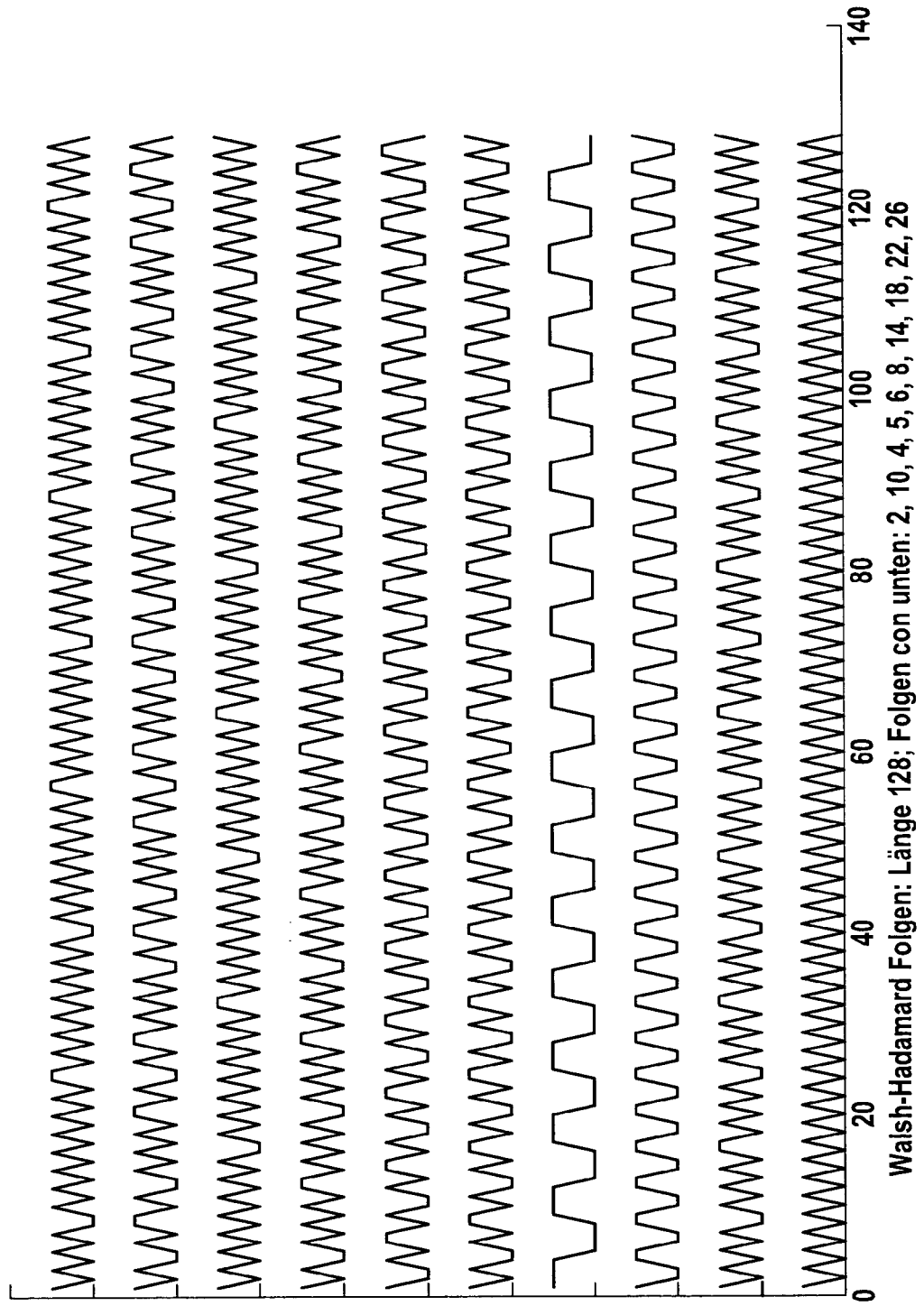
FIG. 15 shows a diagram with Walsh-Hadamard code sequences of the method according to FIG. 14.

FIG. 14 shows an operation diagram of the embodiment of a method according to the present invention. Like the method of FIG. 13, the method of FIG. 14 is a CDMA method. In block 130, a set of code sequence of Walsh-Hadamard code with a length of 128 bits is used to modulate the light of 8 LEDs each with a different Walsh-Hadamard code. FIG. 15 shows examples for Walsh-Hadamard codes. The choice of the appropriate Walsh-Hadamard sequences influences the bandwidth of the modulation signals which are generated. Preferably, the Walsh-Hadamard sequences 2, 6, 8, 10, 14, 18, 22 and 26 are chosen, see FIG. 14, because the lower range of the resulting signal bandwidth is as high as 50 kHz, which is higher than the 10 kHz in the case of the method in FIG. 13 and allows to improve the attenuation of low-frequency noise. Moreover, the complexity of the band-pass can be significantly reduced. The 8 Walsh-Hadamard-codes are preferably stored in the internal memory of the FPGA which performs the signal modulation. Such an internal memory does not need to be large, and in consequence the costs of said FPGA decrease. The 8 LEDs are substantially activated in parallel, by square signals with a reference frequency (carrier) of about 100 kHz.

Shown in block 131 of FIG. 14, said 8 LEDs irradiate, substantially in parallel, one sample receptacle each. Thus, 8 sample radiations are generated in parallel, and converted to a time-dependent electric sum signal (current i(t)) by a photomultiplier, shown in block 131 of FIG. 14. Said current is converted and amplified to a voltage by the transimpedance amplifier, shown in block 132. Said transimpedance amplifier has the characteristic of a highpass, such that low-frequency fractions (=noise, interferences) of the signal are attenuated. The bandpass has the ranges 50 kHz and 900 kHz, corresponding to the bandwidth of the signal, shown in block 133, and is another noise suppression means which improves the sum signal quality. The sum signal is digitized by sampling the analogue sum signal with preferably 400 kHz by a fast analogue/digital transducer, shown in block 134 of FIG. 14. The sampling in block 134 and the averaging in block 135 as well as the signal generation in block 130 are synchronized which is triggered by the signal analysis block 135. A higher number of averaging cycles are preferably used to improve the S/N of the evaluated signals, regarding the overall measuring time which should be short.

The result of the averaging unit in block 135 in FIG. 14 is transferred to the correlation means in block 136 which performs a circular correlation operation using the modulation code sequence as a reference. The method of this embodiment offers in particular the advantage that substantially no floating point operation is required to perform the analysis because it is substantially performed in integer mathematics. Thus, a simple processor unit, e.g. an FPGA, can be used as transformation means to perform the mathematical operation. Moreover, the signal analysis substantially requires addition and subtraction operations while multiplication operations are substantially not needed. Thus, the signal analysis becomes faster than the FFT in the FDMA-method. Moreover, the code sequences are quite short such that a small FPGA, in particular without an external memory device, can be used for the analysis which reduces costs.

Figure 16:
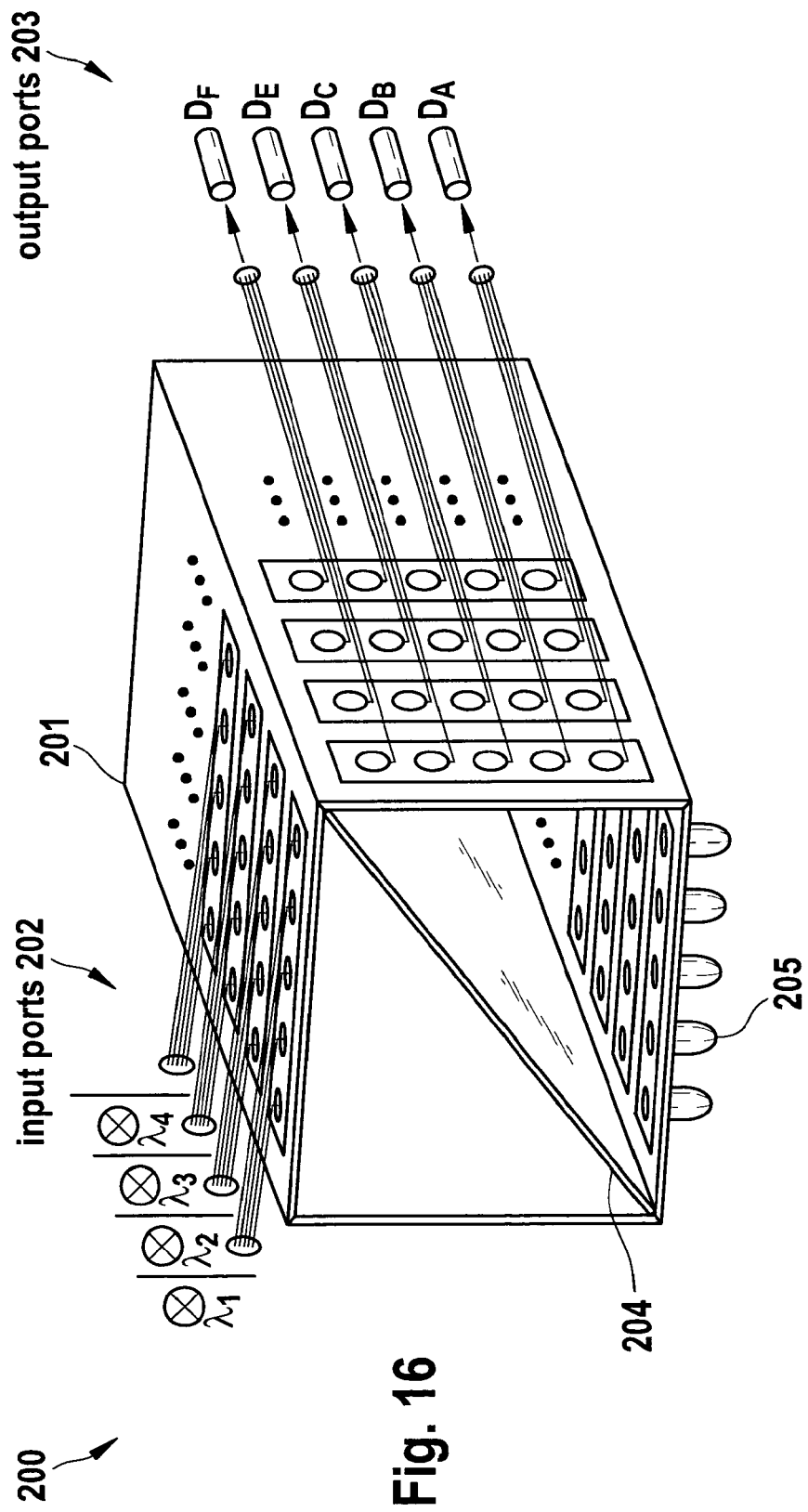
FIG. 16 shows a schematic view of the principle of an optical block of a preferred embodiment of the apparatus according to the present invention.

FIG. 16 shows a schematic view of an optical block of a preferred embodiment of the apparatus according to the present invention. The optical block 200 of the preferred embodiment is adapted to be used with 96-well plates, which have standard geometry. The optical block device allocates space of substantially cuboid shape. The components of the optical device are preferably mounted on a stage 201. The optical block device provides input ports 202, output ports 203, a mirror device 204, comprising at least one dichroic mirror. Even if only a few input ports are shown in FIG. 16, the apparatus in said preferred embodiment comprises a number of x+(n−1) input ports, corresponding to the same number of rows (r>=x) of radiation elements, and further comprises c=y columns of radiation elements, which form an array of radiation elements, which are capable to emit radiation towards the sample containers 205, located on the bottom in FIG. 16. The sample containers 205 are not part of the optical block device. Herein, the radiation elements of each row show the same row-emission spectrum which is one out of said n different emission spectra, referred to as $\lambda_1$, $\lambda_2$ and $\lambda_3$ in FIG. 16, and wherein further m blocks of rows are provided, wherein m−1 blocks have the same sequence of rows with row-emission spectra (r, c, n and m are natural numbers) and one block has said sequence in part. In the embodiment, n=3, m=5 x=12 and y=c=8, even if FIG. 16 shows a differing number of elements for reasons of drawing simplicity. Each input port is adapted to receive the radiation, which is emitted by a radiation source and which is to be transmitted towards a number of c=y radiation elements, which in consequence show the same row-emission spectrum.

The radiation, which is emitted by radiation sources (not shown), is input to said input ports and directed by means of optical fibers to the radiation elements. Each radiation element comprises one emitter element, which comprises the down-stream end face of said optical fiber. Further, each emitter element comprises a lens which improves the focusing of the radiation on a sample container. The radiation is directed downwards to the sample and thereby transmits through the dichroic mirrors 204.

The sample radiation of each sample leaves the respective sample container in upward direction, is reflected by the dichroic mirror 204 and directed by an individual collecting lens to an optical fiber of optical means, which direct said sample radiation towards the detection devices. The apparatus of the preferred embodiment provides a number of c=y (y=8) detection devices, even though FIG. 16 does only show 5 detection devices, drawn as $D_A$, $D_B$ and $D_C$, $D_E$ and $D_F$. With the radiation device and the optical block device of the apparatus according to FIGS. 16 to 19, it is possible to simultaneously irradiate all the 96 samples of the sample holder member and to simultaneously generate a number of 96 sample radiations, which are detected simultaneously in parallel. In particular, it is possible to detect simultaneously by means of only one detection device the radiation of a number of 12 sample radiations.

Figure 19:
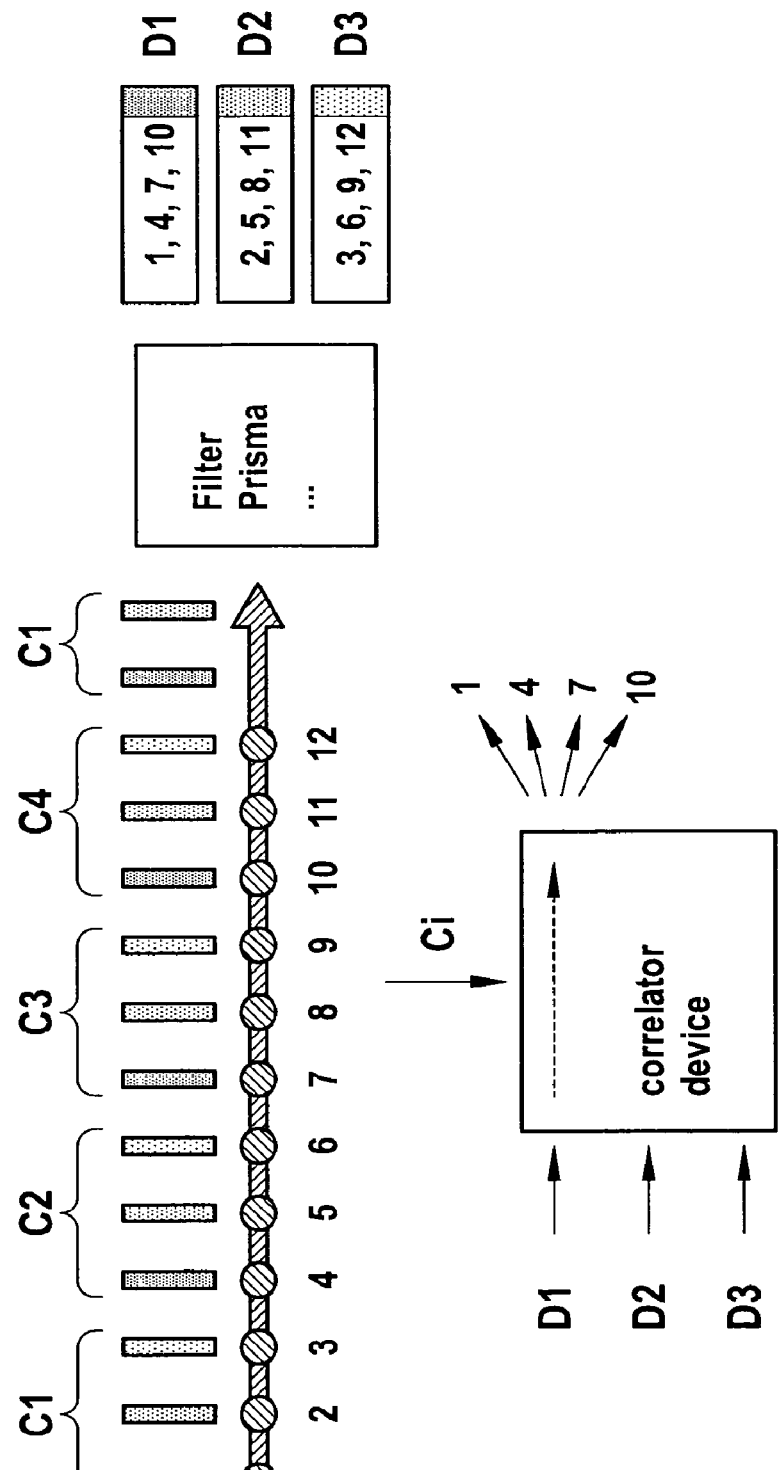
FIG. 19 is a schematic drawing, which shows the decoding scheme of the colour- and code-modulated sample radiations of the preferred embodiment of the apparatus according to the present invention, which is described in FIGS. 16 to 19.

In anticipation of FIG. 19, the twelve sample radiations, which are collected by the optical means, are split into 3 fractions of sample radiations by means of two optical filters, wherein each fraction of sample radiations is based on one colour and comprises the sample radiations of four samples. Due to the code modulation of the radiation, also the respective sample radiation is code modulated and it is therefore possible to distinguish each sample radiation within said fraction of four sample radiations by its individual code modulation. The evaluation of the sum signal, which comprises said four sample radiations, is performed by the evaluation device of the apparatus. The evaluation device comprises a correlator device, which is adapted to correlate the modulation code of each of the four sample radiations with the sum signal, in order to determine the quantity of each individual sample radiation.

Figure 17:
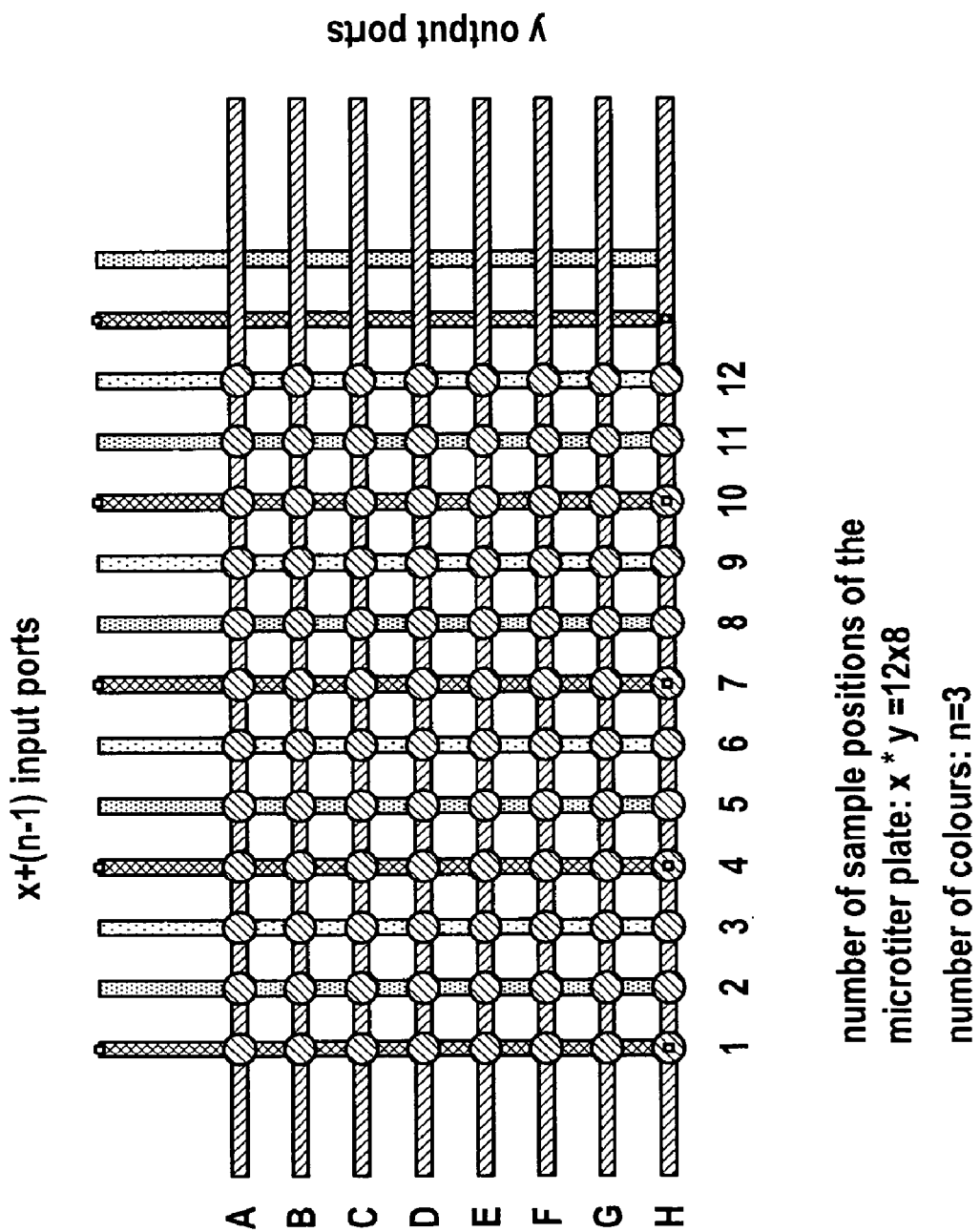
FIG. 17 is a schematic drawing, which shows the schematic arrangement of radiation elements and corresponding sample containers and the arrangement of input and output ports of the preferred embodiment of the apparatus according to the present invention, which is described in FIGS. 16 to 19.

FIG. 17 is a schematic drawing, which shows the schematic arrangement of radiation elements and corresponding sample containers and the arrangement of input and output ports. 14 input ports are provided by the optical block device, wherein each input port is connected to 8 radiation elements. Further, each input port corresponds to one row of the radiation device, which in total comprises 14 rows of radiation elements. Each row of radiation elements has one colour (row emission spectrum). Three colours of radiation elements are provided, wherein the first colour is shown in dark grey, the second colour is shown in middle grey and the third colour is shown in light grey. The array of radiation elements can be further structured into a number of m=5 blocks of radiation elements, wherein a number of m−1=4 blocks shows a sequence of rows of the same colour. For the embodiment, said sequence is dark grey, middle grey, light grey. The rows 1, 4, 7, 10, and 13 of the radiation device of the embodiment correspond to radiation elements, which emit radiation of the colour "dark grey", the rows 2, 5, 8, 11 and 14 correspond to "middle grey", and the rows 3, 6, 9 and 12 correspond to "light grey". The optical block device/radiation device can be automatically, i.e. program driven, into three different positions in relation to the sample holder member.

FIG. 17 shows the first position of the optical block relative to the sample holder member. In the first position, rows 13 and 14 of the radiation device do not irradiate samples. Shifting the radiation device in FIG. 17 to the left by one step with a step size of the distance of two adjacent rows, while keeping the samples 205 in fixed position, allows to row-wise illuminate the samples of each row "x" of the sample holder member with a different colour.

Figure 18:
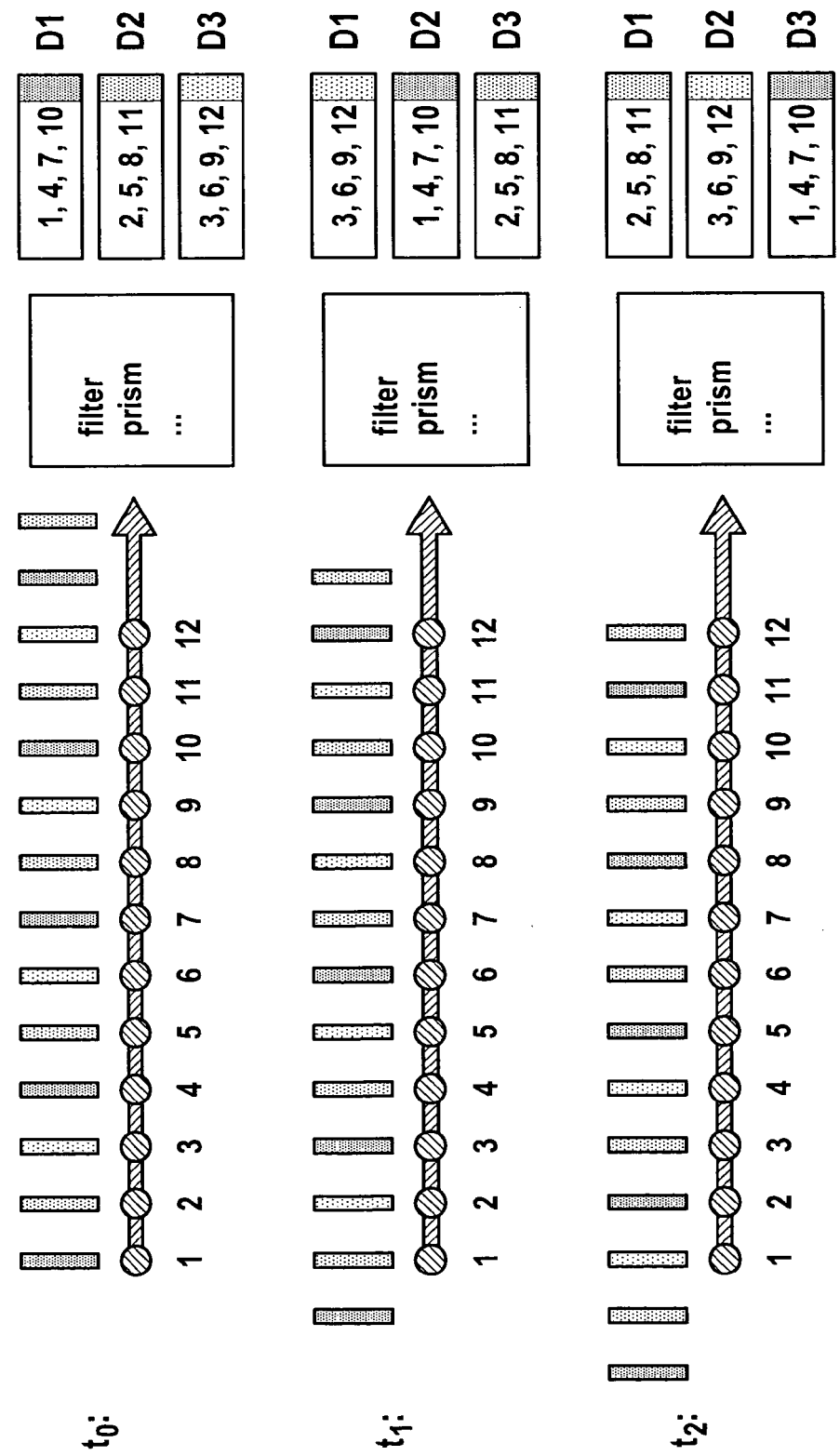
FIG. 18 is a schematic drawing, which shows the position of one column of radiation elements of a radiation device/optical block device at each of three different positions and times $t_0$, $t_1$ and $t_2$ of the preferred embodiment of the apparatus according to the present invention, which is described in FIGS. 16 to 19.

FIG. 18 is a schematic drawing, which shows the position of one column of radiation elements of a radiation device/optical block device at each of said three different positions and times $t_0$, $t_1$ and $t_2$. At time $t_0$, which corresponds to the first position, the rows 13 and 14 of the radiation device do not illuminate samples. The sample radiation, which corresponds to one column of samples and sample containers, is simultaneously collected in one output port from one of the eight output ports A to H. The twelve sample radiations of each output port are split by means of a beam splitter, which can be a filter or prism, to get three fractions of sample radiations, wherein the fraction D1 comprises the sample radiations from rows 1, 4, 7 and 10 (dark grey), the fraction D2 comprises the sample radiations from rows 2, 5, 8, 11 (middle grey) and the fraction D3 comprises the sample radiations 3, 6, 9 and 12 (light grey). In an according manner, at the second position or second time $t_1$ the fraction capital D1 of dark grey colour corresponds to the sample rows 3, 6, 9 and 12, the middle grey colour corresponds to the sample rows 1, 4, 7 and 10 and the light grey colour fraction D3 corresponds to the sample 2, 5, 8 and 11. Analogical, at the third position and in the third time $t_2$ the sample radiations are received as three fractions D1, D2 and D3.

FIG. 19 is a schematic drawing, which shows the evaluation scheme of the sample radiations, which are simultaneously received in one output port. Said sample radiations form a radiation, which is composed of different spectral fractions and which contains several code-modulated sample radiations. The evaluation is shown exemplary for the sample radiations of one column of sample containers, when the radiation device is arranged in said first position, which corresponds to the time $t_0$ in FIG. 18. Fractions D1, D2 and D3, which each comprise four sample radiations, are detected by corresponding detector units D1, D2, and D3. Each detector unit generates a sum signal, which corresponds to—and contains—four sample radiations, which were substantially simultaneously emitted by the samples during the same time periods. FIG. 19 indicates, that the radiation of each block of radiation elements of the radiation device is assigned to an individual code modulation. Block 1 of the radiation device, which comprises the rows 1, 2, and 3 of radiation elements, is assigned to a code C1, block 2 is assigned to code C2, block 3 is assigned to code C3, block 4 is assigned to code C4 and block 5 is again assigned to code C1.

It should be noted, that in principal it would be possible to omit spectral composition/decomposition by using only one colour (row emission spectrum) and to use 12 different codes for the code modulations in order to distinguish 12 different sample radiations. Further, it would be possible in principal to use a larger number of codes for detecting more than four sample radiations by one detection unit. However, using the spectral decomposition method in combination with the code multiplexing method according to the embodiment allows to reduce the number of sample radiations in one sum signal from twelve to four, which has to be detected by one detector as one sum signal. Thus, the available detector dynamics can be utilized more efficiently and therefore, the signal to noise ratio of the evaluated individual signal is improved.

In the embodiment, the apparatus, in particular its optical block device, and the method of detection and evaluation of the signal state a reliable apparatus and method respectively, which in particular require only two positioning steps of the radiation device respective to the sample holder member in order to perform a complete scan of all samples of a multiwell plate. Errors, which arise from a frequent re-positioning of a scanning unit, known from prior art devices, are thus avoided and the overall measuring time is reduced due to the reduced number of positioning periods.

The invention claimed is:

1. Method for radiometrically investigating N (N is a natural number with N>1) sample radiations of at least two samples, which are caused by the radiation of N emitter elements of at least one radiation element wherein said N emitter elements are emitting radiation during time periods which at least partially overlap, wherein the sample radiation is fluorescent light, comprising the steps:
   determining a set of N basic frequencies,
   adding one reference frequency to each of said basic frequencies wherein said reference frequency is higher than each of said basic frequencies,
   using the N sums of the reference frequency and of the basic frequency to provide N modulation signals wherein each modulation signal is used to modulate the radiation of a different emitter element,
   detecting the N sample radiations as a sum signal wherein each sample radiation is modulated according to the modulated radiation which caused the respective sample radiation,
   demodulating the sum signal by using a demodulation method,
   performing a transformation to transfer the demodulated sum signal from a time dependent signal into a frequency dependent signal, and
   determining the quantity of at least one individual sample radiation from the amplitude of said frequency dependent signal in dependence of the basic frequency.

2. Method according to claim 1 characterized in that the N basic frequencies are chosen from a frequency range of 0 kHz to 1 MHz.

3. Method according to at least one of the previous claims characterized in that the reference frequency is at least as high as each of said basic frequencies multiplied by 2.

4. Method according to claim 2 characterized in that said N basic frequencies are chosen from a frequency range of 0 kHz to 4 kHz.

5. Method according to claim 1 characterized in that it further comprises a step of digitizing said sum signal and/or a step of digitizing said demodulated sum signal by sampling and A/D-converting.

6. Method according to claim 1 characterized in that it further comprises a step of averaging said sum signal and/or a step of averaging said demodulated sum signal over the time.

7. Method according to claim 1 characterized in that it further comprises a step of filtering said sum signal by a digital high-pass filter prior to demodulation.

8. Method according to claim 1 characterized in that the demodulation method demodulates said sum signal by multiplying it with the reference frequency.

9. Method according to claim 1 characterized in that the demodulation method demodulates said sum signal by performing a digital calculating.

10. Method according to claim 1 characterized in that a further step of sub-sampling is performed.

11. Method according to claim 1 characterized in that the reference frequency is chosen from a frequency range of 80 kHz to 120 kHz.

* * * * *

UNITED STATES PATENT AND TRADEMARK OFFICE
CERTIFICATE OF CORRECTION

PATENT NO. : 8,374,802 B2 Page 1 of 1
APPLICATION NO. : 12/675764
DATED : February 12, 2013
INVENTOR(S) : Treptow et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 363 days.

Signed and Sealed this
First Day of September, 2015

Michelle K. Lee
*Director of the United States Patent and Trademark Office*